United States Patent
Hamel et al.

(10) Patent No.: US 6,696,436 B1
(45) Date of Patent: Feb. 24, 2004

(54) B-HOMOESTRA-1,3,5(10)-TRIENES AS MODULATORS OF TUBULIN POLYMERIZATION

(75) Inventors: Ernest Hamel, Bethesda, MD (US); Mark S. Cushman, West Lafayette, IN (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/111,664

(22) PCT Filed: Oct. 12, 2000

(86) PCT No.: PCT/US00/28273
§ 371 (c)(1),
(2), (4) Date: Aug. 16, 2002

(87) PCT Pub. No.: WO01/30803
PCT Pub. Date: May 3, 2001

Related U.S. Application Data

(60) Provisional application No. 60/161,533, filed on Oct. 26, 1999.

(51) Int. Cl.$^7$ ............... A61K 31/55; C07D 487/00; C07C 69/00
(52) U.S. Cl. ............... 514/212.04; 514/529; 514/546; 540/519; 560/139; 568/376; 568/719
(58) Field of Search ............... 514/212.04, 529, 514/546; 540/519; 560/139; 568/376, 719

(56) References Cited

U.S. PATENT DOCUMENTS

| | | |
|---|---|---|
| 3,505,393 A | 4/1970 | Galantay |
| 3,513,204 A | 5/1970 | Galantay |
| 5,504,074 A | 4/1996 | D'Amato et al. ............ 514/182 |
| 5,661,143 A | 8/1997 | D'Amato et al. ............ 514/182 |

OTHER PUBLICATIONS

Mark Cushman et al., *Synthesis of Analogs of 2–Methoxyestradiol with Enhanced Inhibitory Effects on Tubulin Polymerization and Cancer Cell Growth.* J.Med Chem. vol. 40, No. 15, 1997, pp. 2323–2334.

Robert. J. D'Amato et al., *2–Methoxyestradiol, an endogenous mammalian metabolite, inhibits tubulin polymerization by interacting at the colhicine site.* Proc. Natl. Acad. Sci. USA, vol. 91, No. 9, Apr. 1994, pp. 3964–3968.

Gil–Jong Kang et al., *N–Acetylcolchinol O–Methyl Ether and Thiocolchcicine, Potent Analogs of Colchicine Modified in the C Ring.* The Journal of Biological Chemistry, vol. 265, No. 18, Jun. 1990, pp. 10255–10259.

Pascal Verdier–Pinard et al., *A Steroid Derivative with Paclitaxel–Like Effects on Tubulin Polymerization.* Molecular Pharmacology, vol. 57, No. 3, Mar. 2000, pp. 568–575.

Zhiqiang Wang et al., *Synthesis of B–Ring Homologated Estradiol Analogues that Modulate Tubulin Polymerization and Microtubule Stability*, J. Med Chem. vol. 43, No. 12, 2000, pp. 2419–2429.

*Primary Examiner*—Barbara P. Badio
(74) *Attorney, Agent, or Firm*—Leydig, Voit & Mayer, Ltd.

(57) ABSTRACT

The invention provides B-ring expanded estra-1,3,5(10)-triene compounds of general formula (1) which modulate the polymerization of tubulin and/or the depolymerization of microtubules. The compounds have anti-angiogenic and anti-tumor activity. The invention also provides methods of preparing the compounds, and methods of using the compounds for the treatment of cancer or other mammalian diseases characterized by undesirable angiogenesis. The compounds of the invention are also expected to have utility as research tools.

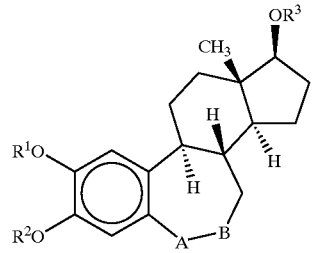

(1)

39 Claims, 7 Drawing Sheets

B-HOMOESTRA-1,3,5(10)-TRIENES AS MODULATORS OF TUBULIN POLYMERIZATION

This application is a 371 of PCT/US00/28273 filed Oct. 12, 2000, which claims benefit of U.S. Provisional Application No. 60/161,533 filed Oct. 26,1999.

FIELD OF THE INVENTION

The present invention relates to the general field of steroid chemistry, particularly to estrone derivatives, and more particularly to B-ring expanded estra-1,3,5(10)-triene compounds. The invention also relates to the field of anti-mitotic, anti-tumor, and anti-angiogenic therapeutics, particularly to the field of therapeutics that function by modulation of the polymerization of tubulin and/or the depolymerization of microtubules.

BACKGROUND OF THE INVENTION

1 Tubulin polymerization and Microtubule Assembly and Disassembly.

Cell mitosis is a multi-step process that includes chromosome replication and cell division. It is characterized by the intracellular movement and segregation of organelles, including mitotic spindles and the replicated chromosomes. Organelle movement and segregation are dependent upon the polymerization of the heterodimeric cell protein tubulin into structures called microtubules. Successful cell division is therefore dependent upon the proper polymerization of tubulin, and also upon the proper functioning and subsequent disassembly of the resulting microtubules.

Tubulin and microtubules are sensitive to a variety of antimitotic drugs. For example, colchicine and nocadazole are anti-mitotic drugs that bind tubulin and inhibit tubulin polymerization, preventing microtubule formation. As such they have anti-tumor activity. In contrast, the anti-cancer drug TAXOL™ binds to and stabilizes the microtubules, inhibiting depolymerization and thereby interfering with the later stages of mitosis. Thus, compounds that inhibit either the polymerization or depolymerization of tubulin are potential antitumor agents. For reviews, see E. Hamel, *Med. Res. Rev.* 16:207–231 (1996) and L. Wang et al., *Cancer Chemother Pharmacol*, 44:355–361 (1999).

Three major pharmacological sites are present on tubulin: the colchicine site, the vinca alkaloid domain, and the "taxoid" site. The latter site is fully developed only in tubulin polymers with a well-defined protofilament substructure. Parness and Horwitz, *J Cell. Biol.* 91:479–487 (1981); Takoudju et al., *FEBS Lett* 227:96–98 (1988).

2. Non-steroidal Modulators of Tubulin Polyimerization.

Colchicine and nocadazole are anti-mitotic drugs that bind tubulin and inhibit tubulin polymerization. When used alone or in combination with other therapeutic drugs, colchicine in particular may be used to treat cancer. See for example PCT application WO 93/03729, and Japanese patent 03240726 (1991). Allocolchicines, with a 7-membered B ring but 6-membered C ring, have been reported, some of which are more active than the corresponding colchicines. Ionio, *Heterocycles* 22:2207–2211 (1984); Kang et al. *J Biol. Chem.* 265:10255–10259(1990)).

There are several cytotoxic vinca alkaloids that operate by the mechanism of inhibition of tubulin polymerization. P. Verdier-Pinard et al., *Biochem. Pharmacol.* 58:959–971 (1999). In particular, the vinca alkaloid vinorelbine (NAVELBINE™) is a potent inhibitor of tubulin polymerization that is currently approved for certain solid tumors. (Piccart, *Cancer Treat. Rev.,* 23:S59 (1997). Cryptophycin is an even more potent inhibitor that is currently under investigation. D. Panda, *Biochemistry,* 36:12948 (1997).

Paclitaxel (TAXOL™) and docetaxel (TAXOTERE™) are examples of the taxane class of antimitotics, which bind to microtubules much more strongly than they do to individual tubulin molecules. They have the effect of accelerating tubulin polymerization, and stabilizing the microtubules against disassembly, which prevents successful completion of the mitotic process. For reviews, see Rowinsky, *Ann. Rev. Med.,* 48:353 (1997), deFurla, *Phytomedicine* 4:273 (1997), and Balasubramanian et al., *Ann. Reports Med. Chem.,* 33:151–162. These compounds are moderately effective against certain solid tumors. A combination of paclitaxel with vinorelbine has recently been approved by the F.D.A.

Compounds with similar biological effects to those of paclitaxel and docetaxel include discodermolide, eleutherobin, sarcodictyin, and the epothilones. These compounds are in various stages of study and/or development as anti-tumor agents.

3. Steroidal Modulators of Tubulin Polymerization.

Among antimitotic agents that appear to bind at the colchicine site are synthetic analogs of estradiol, such as diethylstilbestrol and estramustine, and the major endogenous metabolite of estradiol, 2-methoxyestradiol ("2ME"). See for example R. D'Amato et al., *Proc Natl Acad Sci USA,* 91:3964–3968 (1994); M. Lottering et al., *Cancer Res.* 52:5926–5923 (1992); L. Spicer and J. Hammond, *Mol. and Cell. Endo.* 64:119–126 (1989); S. Rao and Engelberg, *J Exp. Cell Res.* 48:71–81 (1967).

2-Methoxyestradiol (2ME) is a naturally occurring mammalian metabolite of estradiol; it has very low affinity for the estrogen receptor. H. Breuer and R. Knuppen, *Naturwissenschafte* 12:280–281 (1960); H. Gelbke and R. Knuppen, *Steroid Biochem.,* 7:457–463 (1976). Interest in 2ME has been stimulated by its cytotoxicity in cancer cell cultures, which is characterized by uneven chromosome distribution, faulty spindle formation, inhibition of DNA synthesis and mitosis, and an increase in the number of abnormal metaphases. J. Seegers et al., *J Steroid Biochem.* 32:797–809 (1989); M. Cushman et al,. *J Med. Chem.* 38:2041–2049 (1995).

2ME has been shown to bind to the colchicine binding site of tubulin, resulting in inhibition of tubulin polymerization and/or formation of polymer with altered stability properties and morphology. Hamel et al., *Biochemistry* 35:1304–1310 (1996). Recent in vitro and in vivo results have shown that 2ME inhibits angiogenesis and tumor growth. Fotsis et al., *Nature* 368:237–239 (1994); Klauber et al., *Cancer Res.* 57:81–86 (1997).

Efforts have been made to investigate the structure-activity relationships of 2ME and its analogues, in an effort to design more potent anticancer agents. Most work has been directed at modifications in the steroid A ring, which is presumed to be analogous to the colchicine tropolonic C ring. Among the compounds reported, 2-ethoxyestradiol (2EE) has greater inhibitory effects on tubulin polymerization and is 10-fold more cytotoxic than 2ME. Some 6-substituted 2-ethoxyestradiols were synthesized and also demonstrated promising biological activities. Estradiol analogs bearing acetyl groups at positions C-2 and/or C-17 have also been evaluated for their effects on tubulin polymerization, but had minimal or no effect on tubulin polymerization. H.-M. He and M. Cushman, *Bioorg. Med. Chem. Lett.* 4:1725–1728 1994); M. Cushman et al.,*J. Med. Chem.* 38:2041–2049 (1995); M. Cushman et al., *J. Med. Chem.* 40:2323–2334 (1997).

Miller et al., *J Med. Chem.* 40:3836–3841 (1997) disclosed 7-membered tropolonic A ring analogs of 2ME, which were designed to enhance the similarity of the steroid A ring to the C ring of colchicine. They found several of these A-homoestranes to be highly active inhibitors of tubulin assembly.

4. B-Homoestra-1 .3.5(10)-trienes.

B-Homoestra-1,3,5(10)-trienes are a little-known and very little-studied class of compounds. There have been few reported syntheses of such compounds, and even fewer biochemical or pharmaceutical studies. To the best of the present inventors' knowledge, the five references discussed below constitute the known prior art in this area.

L. W. Rampy, in a thesis entitled "Total Synthesis of B-homoestrone and Approaches to Azaestrones" (1967, University of Michigan, Ann Arbor Mich.; *Chemical Abstracts* 68:96028; *Diss. Abstr.* B 1967, 28(6):2364) described the first total synthesis of racemic "B-homoestrone" (3-hydroxy-B-homoestra-1,3,5(10)-trien-17-one). Eleven intermediates and derivatives having 3-hydroxy and 3-methoxy groups were described. None of the compounds disclosed had more than a single hydroxy or methoxy group on the A ring, and this group was always at the 3-position. No biological or biochemical activity of the compounds was disclosed, although "B-homoestrone" was prepared for the stated purpose of investigating its potential as a modulator of plasma lipid levels.

E. E. Galantay, in French patent 1548354 (1968), disclosed, inter alia, the synthesis in racemic form of B-homoestra-1,3,5(10),8,14-pentaenes, having hydroxy, alkoxy, and acyloxy substituents at position 3. None of the disclosed compounds had more than a single substituent on the A ring, and the substituent was always at the 3-position. The compounds were claimed to be useful for modulating estrogen-dependent conditions, e.g., endometriosis, dysmenorrhea, osteoporosis, and atherosclerosis, but no utility for the treatment of cancer was suggested.

E. E. Galantay and H. P. Weber, *Experientia* (1969) 25(6):571–572, described the total synthesis of racemic "B-homoestrone" and some derivatives, referring to them as "a hitherto unknown class of compounds." These authors were evidently unaware of the previous synthesis of B-homoestrone by L. Rampy. An X-ray crystal structure of the 3-methoxy derivative was reported. None of the compounds disclosed had more than a single methoxy or hydroxy group on the A ring, and this substituent was always at the 3-position. No biological or biochemical activity of the compounds was disclosed.

E. Velarde, L. H. Knox, A. J. Cross, and P. Crabbe, *Justus Liebigs Ann. Chem.* (1971) 748:123–133, described 7-fluoro-B-homoestra-1,3,5(10)-trienes, having hydroxy, methoxy, and acetoxy substituents at position 3. None of the disclosed compounds had more than a single substituent in the A ring, and all were at the 3-position. No biological or biochemical activity of the compounds was disclosed.

M. B. Groen and F. J. Zeelen, *Recl.: J. R. Neth. Chem. Soc.* (1984) 103(5):169–173, described the preparation of 1-methoxy and 3-methoxy B-homo-gona-1,3,5(10)-triene steroids, and subsequent transformations of the D ring to provide 3-methoxy-B-homoestra-1,3,5(10)-trien-17-one. However, none of the compounds described by Groen and Zelen had more than a single methoxy group on the A ring. No biochemical, pharmacological, or biological activity of the compounds was disclosed.

In addition to the synthesis and characterization of B-homoestra-1,3,5(10)-trienes described in the above references, these compounds fall into one of the many large classes of compounds generically represented, but neither prepared nor characterized, in U.S. Pat. Nos. 5,504,074 and 5,661,143. These patents are incorporated herein by reference in their entireties.

5. Summary

Although paclitaxel and docetaxel in particular have proved to be medical and commercial successes, all of the active tubulin- or microtubule-modulating agents described above suffer from toxicity problems, such as bone marrow suppression, hair loss, diarrhea, etc. They also tend to be specific for a limited class of tumor types. There remains a need for newer modulators of tubulin polymerization which may prove to have improved selectivity and reduced side-effects.

BRIEF DESCRIPTION OF THE INVENTION

1. Definitions.

"Diseases characterized by undesirable cell mitosis" includes but is not limited to excessive or abnormal proliferation of endothelial cells (e.g., psoriasis, atherosclerosis, endometriosis, hyperplasias), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis.

"Diseases characterized by undesirable angiogenesis" includes but is not limited to hematomas, and angiogenesis accompanying: solid tumors, rheumatoid arthritis, psoriasis, diabetic retinopathy and other ocular angiogenic diseases such as retinopathy of prematurity (retrolental fibroplasic), macular degeneration, corneal graft rejection, neovascular glaucoma and Osler Weber syndrome. Normal but undesired processes involving angiogenesis, such as menstruation and the implantation of a blastula, are intended to fall within the meaning of the phrase as well.

The terms "alkyl" and "acyl" as used herein are intended to include both straight-chain and branched alkyl and acyl groups.

"MAP(s)" refers to microtubule-associated protein(s), as described in E. Hamel and C. Lin, *Biochemistry*, 23:4173–4184 (1984).

2. Description of the Invention

It has been discovered that certain compounds within the scope of the claims below modulate tubulin polymerization and microtubule formation and/or depolymerization, and therefore are expected to be useful for treating mammalian diseases characterized by undesired cell mitosis and/or undesired angiogenesis.

One object of this invention is to provide B-ring expanded estra-1,3-5(10)-triene derivatives of formula 1:

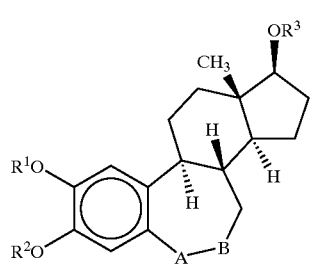

wherein the groups $R^1$, $R^2$, $R^3$, A and B are as described further hereinbelow.

Another object of the invention is to provide pharmaceutical compositions comprising the compounds of the invention, and methods of treating mammals in need of anti-tumor or anti-angiogenic therapy with these compositions.

Yet another object of the invention is to provide methods of making 2,3-disubstituted B-homoestra-1,3,5(10)-trienes of formula 1.

DETAILED DESCRIPTION OF THE INVENTION

Figure 1A:
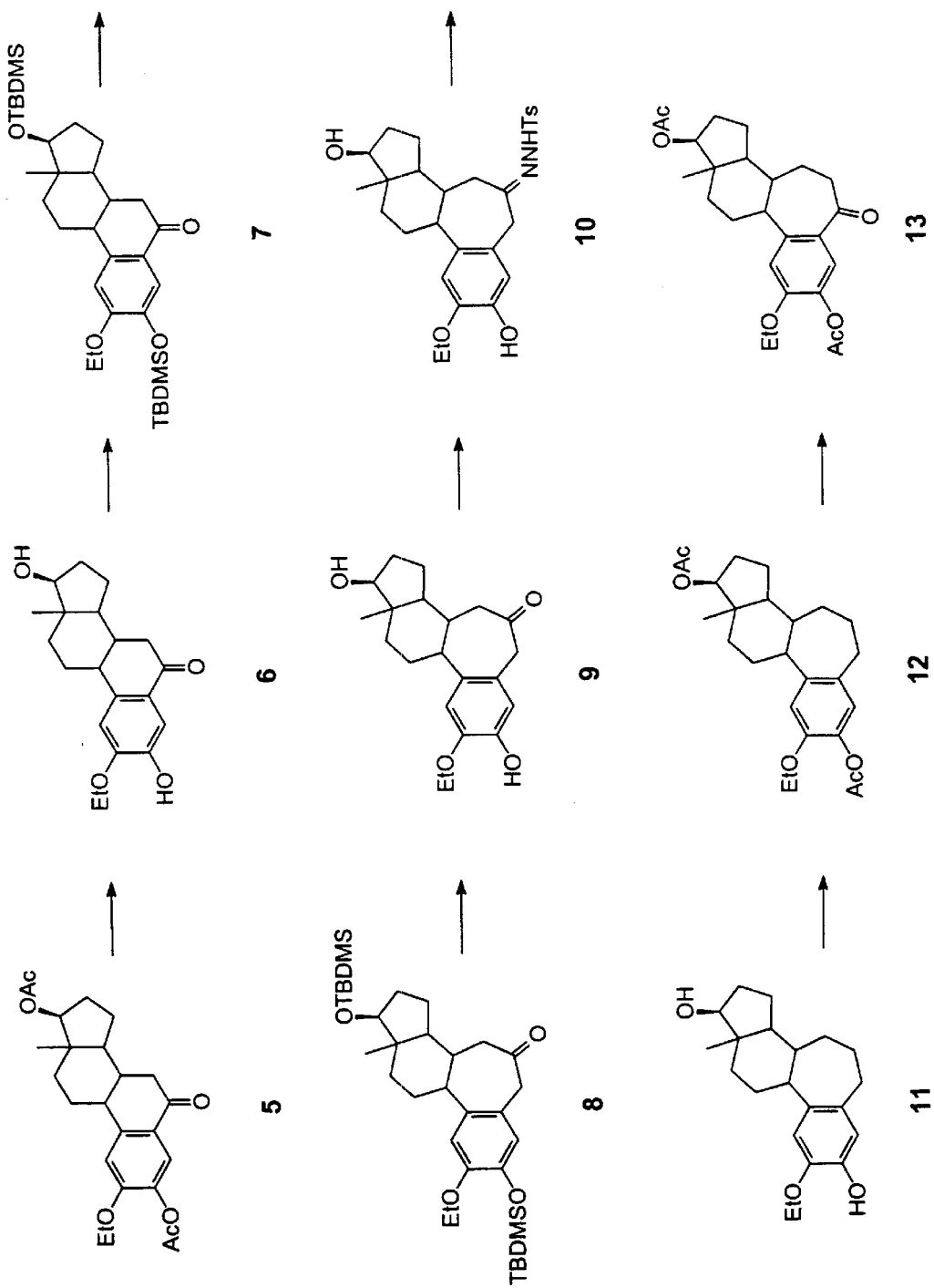
FIGS. 1A and 1B illustrate methods of preparing certain representative compounds of the invention, where the group A is CH2 or C—O.

In previous work, protected estradiol analogs bearing acetyl groups at positions C2 and/or C17 have been evaluated for their effects on tubulin polymerization. Invariably, these compounds had minimal or no effect on s polymerization (M. Cushman et al., *J Med. Chem.* 38:2041–2049 (1995); M. Cushman et al., *J. Med. Chem.* 40:2323–2334 (1997)). Nonetheless, compounds 13 and 18 of the present invention have been found to stimulate microtubule assembly in a manner qualitatively similar to that observed with the potent anticancer drug paclitaxel. Also surprisingly, compounds such as 11, 29, and 32 of the present invention have been found to inhibit tubulin polymerization. The presence of inhibitors and stimulators of tubulin polymerization within a single class of compounds is a novel and unexpected observation.

Accordingly, this invention provides compounds having the following structure:

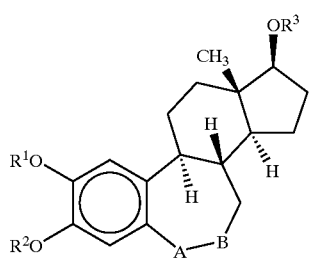

1 wherein A is $CH_2$, $NR^4$, C=O, C=NOH, CHOH ,or $CHNHCR^5$; B is $CH_2$ or C=O; $R^1$ is H, methyl, ethyl, n-propyl, i-propyl, cyclopropyl, cyclopropylmethyl, 1-propenyl, allyl, or vinyl, or other $C_1$ to $C_6$ alkyl, cycloalkyl, or alkenyl group; $R^2$ and $R^4$ are independently H, methyl, ethyl, n-propyl, i-propyl, acetyl, propionyl, butyryl, cyclopropanecarbonyl, or isobutyryl, or other $C_1$ to $C_6$ alkyl, acyl, or cycloalkyl group; $R^3$ is H, acetyl, propionyl, butyryl, cyclopropanecarbonyl, or isobutyryl, or other $C_1$ to $C_6$ acyl group; and $R^5$ is H, methyl, ethyl, n-propyl, i-propyl, acetyl, propionyl, butyryl, cyclopropanecarbonyl, or isobutyryl, or other $C_1$ to $C_6$ alkyl, acyl, or cycloalkyl group In preferred embodiments, A is C=O, CHOH, or CHNH-COR; B is $CH_2$; $R^1$ is selected from the group consisting of H, methyl, ethyl, 1-propenyl, n-propyl, and i-propyl; $R^2$ and $R^4$ are selected from the group consisting of H, methyl, ethyl, n-propyl, i-propyl, acetyl, propionyl, butyryl, and isobutyryl; $R^3$ is selected from the group consisting of H, acetyl, propionyl, butyryl, and isobutyryl; and $R^5$ is selected from the group consisting of H, acetyl, propionyl, butyryl, and isobutyryl.

Another group of preferred compounds are those wherein A is $NR^4$ and B is C=O.

More preferably, A is C=O or CHNHCOR; B is $CH_2$, $R^1$ is selected from the group consisting of methyl, ethyl, and 1-propenyl; $R^2$ is selected from the group consisting of H, acetyl, propionyl, butyryl, and isobutyryl; and $R^3$ is selected from the group consisting of acetyl and propionyl.

Most preferably, A is C=O, B is $CH_2$, $R^1$ is selected from the group consisting of methyl, ethyl, and 1-propenyl; $R^2$ is selected from the group consisting of H and acetyl; and $R^3$ is selected from the group consisting of acetyl and propionyl.

The compounds of this invention exhibit unexpected properties with respect to their effect on polymerization of tubulin. In particular, depending upon the identities of the groups $R^2$, $R^3$, A, and B, the compounds either inhibit or enhance polymerization. For example, where $R^1$ is ethyl, $R^2$ and $R^3$ are H, and A and B are $CH_2$, the compound inhibits tubulin polymerization. Where $R^1$ is ethyl, $R^2$ and $R^3$ are $COCH_3$, A is C=O, and B is $CH_2$, on the other hand, the compound stimulates tubulin polymerization and stabilizes microtubules.

By the methods provided herein, and by obvious modifications thereto, the compounds of this invention may be prepared from the appropriate starting materials. It will be appreciated that where A is CHOH or $CHNHR^4$, the compounds may exist as either the α or β isomer at C-6, or as a mixture of the two compounds. Similarly, where B is CHOH, the compounds may exist as either the α or β, isomer at C-7. It is intended that pure isomers, and mixtures thereof, are within the scope of the claims. The compounds are presented merely by way of example, and are not intended to limit the scope of the invention.

Figure 1B:
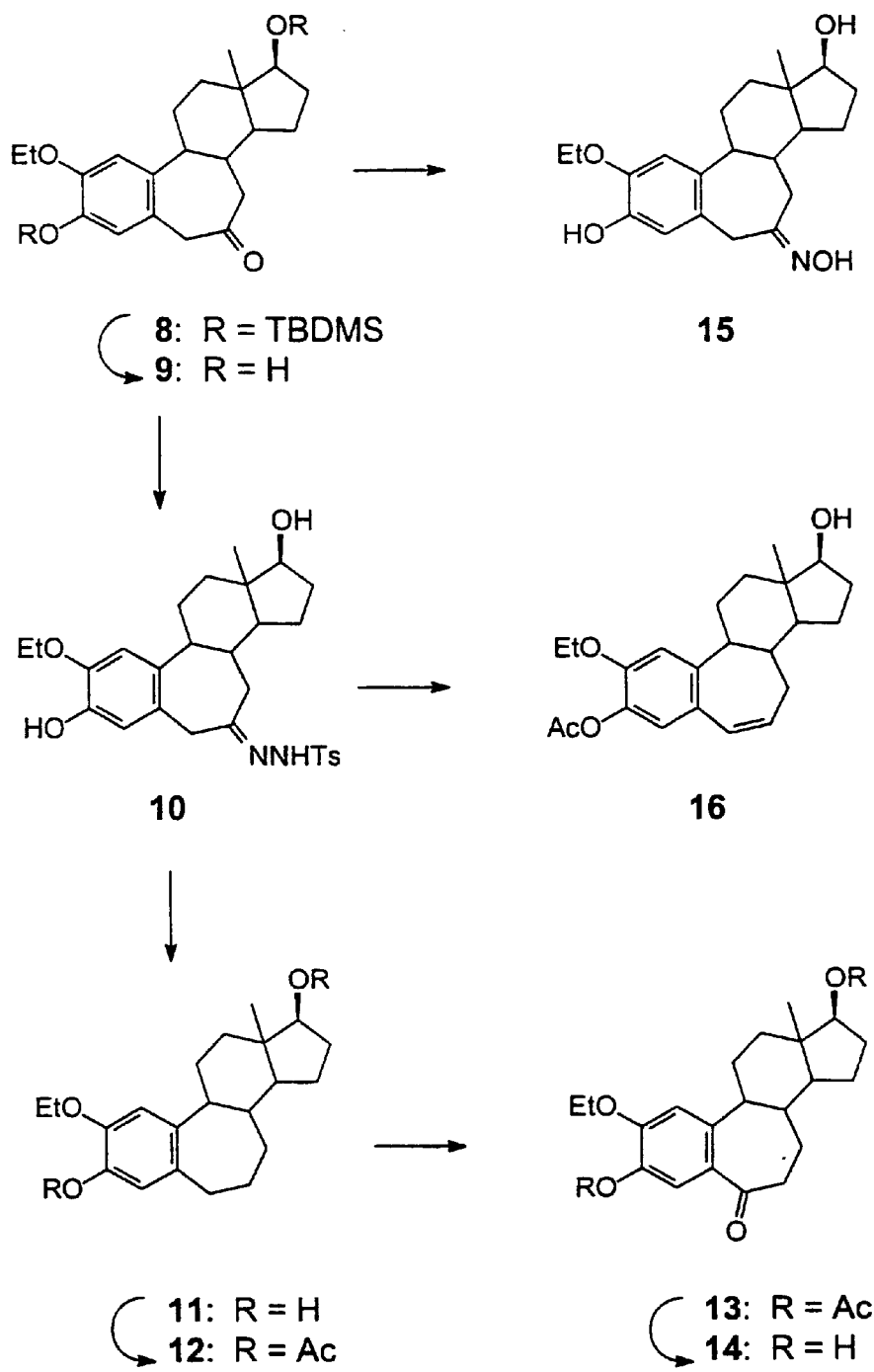
Figure 2:
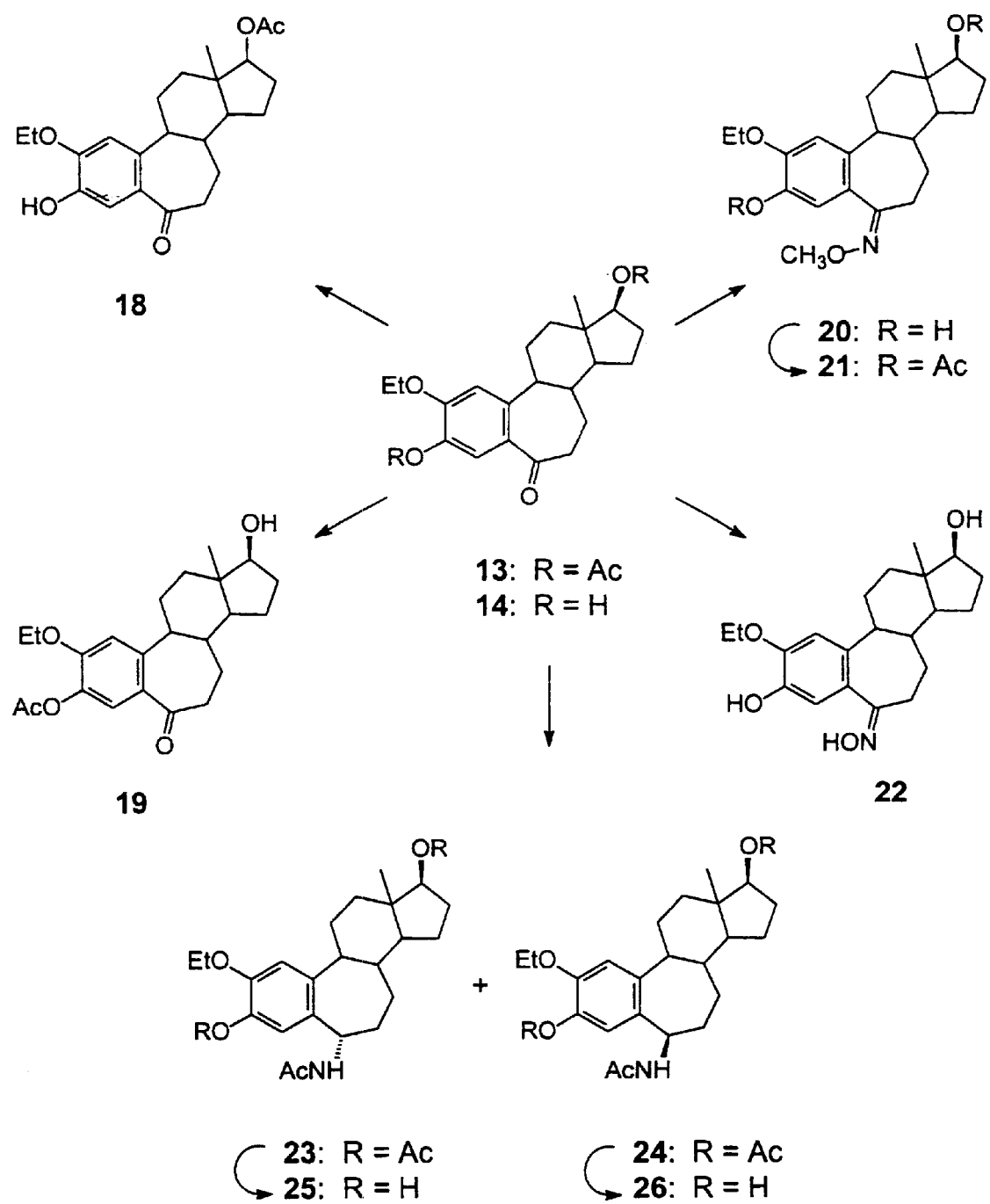
FIG. 2 illustrates a method of preparing certain representative compounds of the invention, where the group A is CHNHCOR
Figure 3:
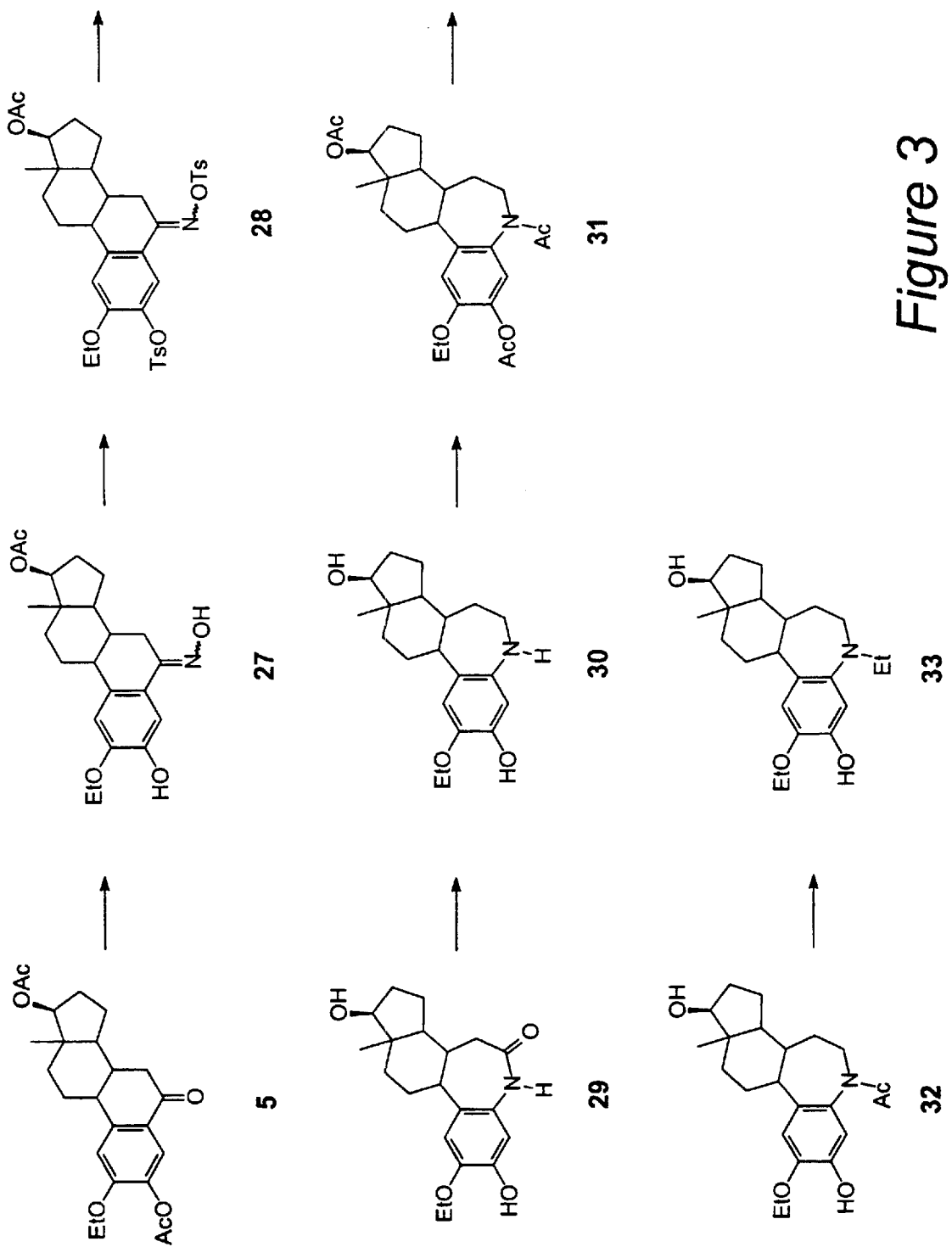
FIG. 3 illustrates a method of preparing certain representative compounds of the invention, where the group A is $NR^4$.

Another object of this invention is to provide methods of making the compounds of the invention. The compounds may be prepared from commercially available steroids by the method outlined in Scheme 1 (FIG. 1). Conversion of commercially available "β-estradiol" (estra-1,3,5(10)trien-3,17β-diol) to 3,17-dialkoxyestra-1,3,5(9)trien-2-ols can be carried out by a published procedure; see Z. Wang and M. Cushman, *Synthetic Commun.* 28:4431–4437 (1998). Various protecting groups for the 3- and 17-hydroxyl groups, such as benzyl, silyl, and the like, may be employed as desired if they are compatible with subsequent operations.

In the example provided, 3,17β-bis(methoxymethoxy) estra-1,3,5(10)trien-2-ol is first treated with an alkylating agent, such as an alkyl halide or alkanesulfonate, in the presence of an appropriate base. In the example provided, alkylation with iodoethane gives 2. Deprotection of 2 under appropriate conditions provides the intermediate 3. Acylation of the two hydroxyl groups in 3 provides 4, and oxidation at the benzylic 6-position with chromium trioxide in acetic acid then provides a 6-oxo intermediate such as 5. Use of other acylating agents, such as acyl chlorides and anhydrides, or use of carboxylic acids in the presence of an activating agent, provides other embodiments with the desired identities of $R^2$ and $R^3$. Where $R^2$ and $R^3$ are desired to be different, a stepwise procedure will selectively introduce $R^2$ first, at the less hindered and more acidic phenolic oxygen. If base-sensitive hydroxyl protecting groups such as acetate are present, they are removed, for example by treatment with ammonia or an alkali metal hydroxide, and the hydroxyl groups are protected with base-stable protecting groups such as t-butyldimethylsilyl ethers. In the present examples, the result is compound 7.

A key step in the method of synthesis of this invention is the B ring homologation of an estra-1,3,5(10)-triene-6-one, which is not readily accomplished by the usual methods. It has been found that estra-1,3,5(10)-triene-6-ones do not behave in a predictable fashion when traditional ring-expansion reactions are attempted. After many unfruitful attempts, including for example attempted Tiffeneau-Demjanov rearrangements and diazomethane reactions, it has been found that two more modem procedures, Taguchi's method and the TMSCHN$_2$/Et2O.BF3 method, could provide the desired one carbon ring-expansion products. However, even these methods generated unexpected regiochemical results, as described below.

Taguchi's method involves a two-step sequence: nucleophilic addition of dibromomethyllithium to a carbonyl group at C-6, followed by addition of a strong base to generate a β-oxido carbenoid, which rearranges to a ring-expanded lithium enolate. See Taguchi et al., *J. Am. Chem. Soc.* 96:6510–6511 (1974); idem., *Bull. Chem. Soc. Japan* 50:1592–1595 (1977).

Treatment of compound 7 by Taguchi s method, using lithium diisopropylamide as base in the first step, gave the B-ring expanded product 8, in which aryl migration had occurred to leave the ketone at the 7-position. The observed regioselectivity is entirely unexpected for this type of compound, in view of the fact that when Taguchi and coworkers used benzaldehyde to study this reaction, they obtained exclusively the hydrogen migration product.

The problem was solved by relocating the carbonyl group from the 7-position to the 6-position. The carbonyl group in 8 was reduced to methylene with 80% yield by the method of Kabalka and Baker, *J. Org. Chem.* 40:1834–1835 (1975), involving reduction of tosylhydrazone 10 with catecholborane followed by thermal decomposition. After acetylation of the two hydroxyl groups of 11, oxidation of 12 with chromium trioxide in acetic acid proceeded selectively at the 6-position to give 3,17β-diacetate 13. Saponification then provided B-homo-3,17β-dihydroxy-2-ethoxyestra-1,3,5 (10)-triene-6-one 14.

Alternatively, the ring enlargement of 6 directly to 14 may be accomplished by using trimethylsilyldiazomethane and boron trifluoride etherate (TMSCHN$_2$/Et$_2$O.BF$_3$) by the method of Seto et al., *Tetrahedron Lett.,* 40:2359–2362 (1999). Seto et al. homologated 6-oxo-steroids to give selectively B-homo-6-oxo-steroids in ca. 80% isolated yield. However, reaction of ketone 5 with TMSCHN$_2$ in the presence of Et$_2$O.BF$_3$ at −20° C. followed by acid treatment gave an inseparable mixture of B-ring homologated estradiol derivatives (13 and its 7-oxo isomer). The NMR spectrum indicated the presence of an equimolar mixture of the two ketones, but all attempts to separate these two isomers were unsuccessful. This problem was solved by removal of the acetyl groups, after which the B-homoestradiol compounds 14 (24%) and 9 (31%) could be isolated by column chromatography.

The reductive amination of compound 14, followed by acylation, is an effective approach to the respective acetamides. The 6α-epimer 23 and 6β-epimer 24 could be isolated by flash chromatography on silica gel using a suitable solvent system with careful operation. The ratio of the respective isomers obtained from the reductive amination were found to be 1 (α):2(β). Hydrolyses of 23 and 24 were accomplished with dilute sodium hydroxide solution in methanol, which removed the 3 and 17 acetyl groups to afford the corresponding 25 and 26, respectively.

Extensive NMR analysis of compounds 25 and 26 was performed in order to elucidate their structure, absolute configuration and conformation. The stereochemistry at C-6 in 25 and 26 was deduced by NOESY experiment. A very strong NOE between H-6 and H-9 was observed in the spectra of 26, which was absent in the spectra of 25. The assigned C-6 configurations were confirmed by X-ray crystallography.

The mono-protected B-homoestra-1,3,5(10)-trien-3,17-diols bearing one acyl group at the 17-position (e.g., 18) or at the 3-position (e.g., 19) are prepared by selective hydrolysis of a phenolic ester such as 13 or by selective acylation of the phenolic group of a 3,17-diol such as 14. Thus, mild basic hydrolysis of compound 13 with KHCO$_3$ in methanol at 65° C. for 1.5 hr provided the 17-βmonoacetate 18, while treatment of 14 with 1-acetyl-1H-triazolo[4,5-b]pyridine and 1 N NaOH in THF provided the monoacetate 19 in high yield. The 6-ketones of this invention, for example 13, 14, and 18, can be transformed to oximes, for example 21, 21 or methoximino compound 22, by treatment with the appropriate hydroxylamine or alkoxylamine. The 6,7-dehydro compound 16 was prepared by the treatment of compound 10 with methyllithium in anhydrous THF.

Compounds of this invention where A is NR can be prepared by rearrangement of a 6-oximinoestra-1,3,5-(10)-triene. A preferred method is by base-catalyzed rearrangement of a 6-(O-arylsulfonyloximino) derivative, for example the rearrangement of a 6-(O-toluenesulfonyloximino) derivative such as 28 catalyzed by basic alumina. The resulting B-ring lactam 29 may be reduced, alkylated, acylated, etc. by well-known methods, providing for example compounds such as 30–33.

It is anticipated that prodrug forms of the compounds of this invention will prove useful in certain circumstances, and such compounds are intended to fall within the scope of the invention. Prodrug forms may have advantages over the parent compounds of formula 1 in that they are better absorbed, better distributed, more slowly metabolized or cleared, etc. Prodrug forms may also have formulation advantages in terms of crystallinity or water solubility. For example, compounds of the invention having one or more hydroxyl groups may be converted to esters or carbonates bearing one or more carboxyl, hydroxyl or amino groups, which are hydrolyzed at physiological pH values or are cleaved by endogenous esterases or lipases in vivo. See for example U.S. Pat. Nos. 4,942,184, 4,960,790, 5,817,840, and 5,824,701 (all of which are incorporated herein by reference in their entirety), and references therein.

Another object of this invention is to provide a method of treating an individual with cancer, or another disease characterized by undesirable angiogenesis, with compounds of formula 1. The method of the invention comprises administering to an individual a therapeutically effective amount of at least one compound of formula 1, or a prodrug thereof, which is sufficient to inhibit tumor growth.

The dose of the compound used in the treatment of such disease will vary in the usual way with the weight and metabolic health of the patient, and with the relative efficacy of the compound employed when used against the type of tumor involved. The preferred initial dose for the general patient population will be determined by routine dose-ranging studies, as are conducted for example during clinical trials. Therapeutically effective doses for individual patients may be determined by titrating the amount of drug given to the individual to arrive at the desired therapeutic effect without incurring an unacceptable level of side effects, as is currently done with other forms of chemotherapy.

For example, the compound 11 would be expected to be useful at dosages which are about 3 to 5 times those used for taxotere. A preferred initial dose for this compound, accordingly, may be estimated to be between about 10 and 2000 mg/day for an adult human, more preferably between 100 and 1000 mg/day. The initial dose may be varied so as to obtain the optimum therapeutic effect in the patient, and may be provided as a daily dose, in a divided dose regimen, or by continuous infusion.

Administration of the compounds of this invention may be by any method used for administering therapeutics, such as for example oral, parenteral, intravenous, intramuscular, subcutaneous, or rectal administration.

This invention also provides pharmaceutical compositions useful for providing anti-tumor activity, which comprise at least one compound of the invention. In addition to comprising at least one of the compounds described by formula 1 or a pro-drug thereof, the pharmaceutical composition may also comprise additives such as preservatives, excipients, fillers, wetting agents, binders, disintegrants, buffers, and/or carriers. Suitable additives may be for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulfate.

In addition to unit dose forms, multi-dosage forms are also contemplated to be within the scope of the invention. Delayed-release compositions, for example those prepared by employing slow-release coatings, micro-encapsulation, and/or slowly-dissolving polymer carriers, will also be apparent to those skilled in the art, and are contemplated to be within the scope of the invention. For example, the compounds of this invention may be incorporated into biodegradable polymers allowing for sustained release, the resulting compositions preferably being implanted where delivery is desired, for example, at the site of a tumor. Biodegradable polymers suitable for this embodiment are well-known in the art, see for example Brem et al., *J. Neurosurg.* 74:441–446 (1991). The compounds of this invention may be also be incorporated into other sustained-release formulations, such as those employing coated particles. See for example U.S. Pat. No. 5,968,551 and references therein.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerin, propylene glycol, or ethyl alcohol; preservatives, for example methyl or propyl p-hydroxybenzoate or sorbic acid; and if desired conventional flavoring or coloring agents.

For parenteral administration, which will be a preferred route of administration in the hospital or cancer clinic environment, fluid unit dosage forms are prepared utilizing the compound and a sterile vehicle. Depending on the concentration used, the compound can be either suspended or dissolved in the vehicle. In preparing solutions the compound can be dissolved in water or saline for injection and filter sterilized before filling into a suitable vial or ampoule and sealing. Advantageously, additives such as a local anaesthetic, a preservative and buffering agents can be dissolved in the vehicle. Suitable buffering agents are, for example, phosphate and citrate salts. To enhance the stability, the composition can be frozen after filling into the vial and the water removed under vacuum.

Parenteral suspensions are prepared in substantially the same manner, except that the compound is suspended in the vehicle instead or being dissolved, and sterilization accordingly cannot readily be accomplished by filtration. The compound can be sterilized by filtration of an alcohol solution, or by other conventional means, for example by exposure to radiation before or after being suspended in the sterile vehicle. Advantageously, a surfactant or wetting agent is included in the composition to facilitate uniform distribution of the compound and stability of the suspension.

All references cited in this disclosure are incorporated by reference herein, in their entirety.

EXAMPLES

Melting points were determined in capillary tubes on a Mel-Temp apparatus and are uncorrected. $^1$H NMR spectra were recorded on a Varian VXR-300S spectrometer using TMS as an internal standard; Cl mass spectra were obtained on a Finnegan 4000 spectrometer; El mass spectra on a Kratos MS50 spectrometer; IR spectra on a Perkin Elmer 1600 series FTIR. Microanalyses were performed at the Purdue Microanalysis Laboratory.

Flash column chromatography was carried out using Merck silica gel (230–400 mesh). Analytical thin-layer chromatography (TLC) was performed on prescored silica gel GF coated glass plates (Analtech; 2.5×10 cm with 250 $\mu$M layer), and spots were visualized with UV light at 254 nm or with 5% $H_2SO_4$ in ethanol. Most chemicals and solvents were analytical grade and used without further purification. Commercial reagents were purchased from Aldrich Chemical Company (Milwaukee, Wis.).

3,17$\beta$-Bis(methoxymethoxy)-2-ethoxyestra-1,3,5-triene (2). A solution of 3,17$\beta$-bis(methoxymethoxy)estra-1,3,5-triene-2-ol (Z. Wang and Cushman, *Synzthetic Commun.* 28:4431–4437 (1998)) (11.3 g, 27.8 mmol) in anhydrous ethanol (225 ml) containing anhydrous potassium carbonate (38.4 g, 280 mmol) was stirred at room temperature under argon for 10 min. Iodoethane (43.7 g, 280 mmol) was introduced to the reaction mixture. The resulting mixture was stirred at gentle reflux. After 4 hr, another portion of iodoethane (10.92 g, 70 mmol) was introduced and the reflux was continued for another 10 hr. The reaction mixture was cooled to room temperature and filtered. The solid was washed with ether (100 ml), and the filtrates were combined and evaporated to dryness. Chromatography of the residue (silica gel 230–400 mesh, ethyl acetate:hexane 1:7 by volume) gave the pure 2 (10.45 g, 92%) as a colorless oil: $^1$H NMR (CDCl$_3$) $\delta$6.85 (s, 2 H), 5.18 (s, 2 H), 4.66 (ABq, J=6.6 Hz, $\Delta$v=3.4 Hz, 2 H), 4.08 (q, J=7.0 Hz, 2 H), 3.61 (t, J=8.5 Hz, 1 H), 3.52 (s, 3 H), 3.38 (s, 3 H), 2.79 (m, 2 H), 2.30–1.20 (m, 13 H), 0.82 (s, 3 H); CIMS (isobutane) m/z (rel intensity) 405 (MH+, 39), 343 (100). Anal. Calcd. for $C_{24}H_{37}O_5$: C, 71.26; H, 8.97. Found: C, 71.48; H, 9.14.

2-Ethoxyestra-1,3,5(10)-triene-3.17$\beta$-diol (3). To a solution of 2 (6.0 g, 14.8 mmol) in THF (100 ml) was added 6 N HCl (100 ml) at room temperature and the resulting solution was stirred at room temperature for 6 hr. The reaction mixture was poured into brine (200 ml) and the products were extracted with ethyl acetate (3×100 ml). The ethyl acetate layers were washed with saturated sodium bicarbonate (100 ml) and brine (100 ml), combined and dried over sodium sulfate, and evaporated to dryness. Chromatography of the residue (silica gel 230–400 mesh, methylene chloride:ethyl acetate 9:1 by volume) gave compound 3 (4.04 g, 85%), which was crystallized from ethyl acetate/ hexane to afford white crystals: mp 151–150° C. (lit.4 mp 154–155° C.); $^1$H NMR (CDCl$_3$) $\delta$6.95 (s, 1 H), 6.65 (s, 1 H), 4.08 (qd, J=6.8 Hz, J=1.5 Hz, 2 H), 3.73 (t, J=8.4 Hz, 1 H), 2.73 (m, 2 H), 2.30–1.20 (m, 18 H), 0.81 (s,3 H).

3,17$\beta$-Diacetoxy-2-ethoxyestra-1,3,5(10)-triene (4). Acetic anhydride (20 ml, 210 mmol) was added under nitrogen at room temperature to a solution of 3 (3.89 g, 12.3 mmol) in anhydrous pyridine (34 ml). The resulting mixture was stirred at room temperature for 24 hr and then poured into ice/water mixture (200 ml). The product was extracted with ethyl acetate (3×100 ml). The organic layers were washed with water (100 ml), aqueous sodium bicarbonate (100 ml) and brine (2×100 ml), and dried over sodium sulfate. The ethyl acetate layer, on evaporation under reduced pressure, gave compound 4 (4.82 g, 98%), which was crystallized from ethyl acetate/hexane to afford white crystals: mp. 132–133° C. (lit.12 mp 135–136° C.); $^1$H NMR (CDCl$_3$) $\delta$6.95 (s, 1 H), 6.75 (s, 1 H), 4.71 (t, J=8.5 Hz, 1 H), 4.09 (qd, J=6.9 Hz, J=1.5 Hz, 2 H), 2.73 (m, 2 H), 2.36 (s, 3 H), 2.12–2.4 (m, 3 H), 2.10 (s, 3 H), 1.1–2.0 (m, 13 H), 0.85 (s, 3 H).

3,17$\beta$-Diacetoxy-2-ethoxyestra-1,3,5(10)-triene-6-one (5). A solution of chromium trioxide (5.14 g, 51.4 mmol) in 90% glacial acetic acid (50 ml) was added dropwise at 10–12° C. to a mechanically-stirred solution of 4 (4.82 g, 12.03 mmol) in glacial acetic acid (77 ml). After the addition, the resulting mixture was stirred at 10–12° C. for 40 min. The mixture was poured into ice-water mixture (400 ml) and the compounds were extracted with ethyl acetate (300, 200, and 100 ml). The organic layers were washed with brine (2×200 ml), solution of sodium bicarbonate (2×150 ml) and brine (2×200 ml), dried over sodium sulfate and evaporated to dryness. Chromatography of the residue on a silica gel column using 30% ethyl acetate in hexane gave the title compound 5 (3.9 g, 78%), which was crystallized from ethyl acetate/hexane to afford white crystals: mp 193–194° C. (lit.12 mp 195° C.); IR (KBr) 1774, 1736, 1719 (C=O); $^1$H NMR (CDCl$_3$) $\delta$7.75 (s, 1 H), 6.95 (s, 1 H), 4.75 (t, J=8.5 Hz, 1 H), 4.19 (q, J=6.9 Hz, 2 H), 2.85–2.48 (m, 2 H), 2.45–1.1 (m, 19 H), 0.85 (s, 3 H).

3,17$\beta$-Dihydroxy-2-ethoxyestra-1,3,5(10)-trien-6-one (6). Under nitrogen, a 20% solution of potassium hydroxide in methanol (15 ml) was added dropwise at room temperature to a suspension of compound 5 (3.0 g, 7.26 mmol) in anhydrous methanol (60 ml). The resulting mixture was stirred at room temperature for 6 hr. The mixture was neutralized with 3 N HCl and the solvent was removed under reduced pressure. The residue was diluted with water (100 ml) and extracted with ethyl acetate (3×100 ml). The combined organic layer was washed with brine (2×100 ml), and dried over sodium sulfate. Removal of the solvents provided a white solid 6 (2.34 g, 98%), which was then crystallized from ethyl acetate/hexane to afford title compound 6 as white crystals: mp 197–199° C. (lit. 12 mp 194–196° C.); $^1$H NMR (CDCl$_3$) $\delta$7.61 (s, 1 H, 4-aromatic CH), 7.20 (s, 1 H, 1-aromatic CH), 4.44 (q, J=6.9 Hz, 2 H, 2-CH2-), 3.83 (t, J=8.5 Hz, 1 H, 17$\alpha$-H), 2.85–1.40 (m, 20H), 0.97 (s, 3 H, 18-CH3).

3,17$\beta$-Bis(t-butyldimethylsilyloxy)-2-ethoxyestra-1,3,5 (10)-triene-6-one (7). Under argon, a solution of compound 6 (4.92 g, 14.9 mmol), imidazole (12.3 g, 178.4 mmol) and t-butyldimethylchlorosilane (i 3.5 g, 89.6 mmol) in DMF (100 ml) was stirred overnight at room temperature. The reaction mixture was poured into ice/cold sodium bicarbonate solution (250 ml) and the product was extracted with ethyl acetate (200 ml, 150 ml, 100 ml). The organic layers were washed with water (200 ml) and brine (2×100 ml), dried over sodium sulfate and evaporated to dryness. Crystallization of the residue from methanol gave compound 7 (7.6 g, 91%), which was obtained as white crystals: mp 150–151° C.; $^1$H NMR (CDCl$_3$) $\delta$7.51 (s, 1 H), 6.78 (s, 1 H), 4.19 (q, J=6.9 Hz, 2 H), 3.65 (t, J=8.5 Hz, 1 H), 2.85–2.48 (m, 2 H), 2.45–1.1 (m, 19 H), 0.98 (s, 9 H), 0.86 (s, 9 H), 0.72 (s, 3 H), 0.15 (s, 6 H), 0.01 (s, 6 H); CIMS (isobutane) m/z (rel intensity) 559 (MH+, 100). Anal. Calcd for $C_{32}H_{54}O_4Si_2$: C, 68.76; H, 9.74. Found: C, 68.61; H, 9.90. B-Homo-3,17$\beta$-bis(t-butyldimethylsilyloxy)-2-ethoxyestra-1,3,5(10)-triene-7-one (8) Under argon , a well-stirred solution of 7 (6.38 g, 11.41 mmol) and dibromo methane (11.9 g, 68.5 mmol) in dry THF (190 ml) was cooled to −78° C. and then the solution was treated with lithium diisopropylamide mono (tetrahydrofuran) (30.4 ml, 1.5 M solution in cyclohexane, 45.6 mmol) dropwise over a period of 1.5 hr. After stirring 3 hr at the same low temperature, n-butyllithium (60 ml, 1.6 M solution in hexane, 96 mmol) was added to the mixture over a period of 1.5 hr. The resulting red solution was stirred for another 1 hr at −78° C. and 10 min at 0° C., quenched by pouring into ice (150 g), and then extracted with ethyl acetate (3×100 ml). The organic layers were washed with brine (3×100 ml), combined and dried over sodium sulfate, and evaporated to dryness. Chromatography of the residue (silica gel 230–400 mesh, methylene chloride:hexane 7:3 by volume) recovered the starting material 7 (1.98 g) and gave the title compound 8 as an oil (2.78 g, 61.6% based on the consumption of 7). Even if large excess of reagents were used, about 25–30% of starting material was recovered in most cases. IR (KBr, cm$^{-1}$) 2955, 2930, 1709 (7-C=O), 1511; $^1$H NMR (CDCl$_3$) δ6.78 (s, 1 H), 6.60 (s, 1 H), 4.04 (qd, J=7.0 Hz, J 1.5 Hz, 2 H), 3.66 (t, J=8.5 Hz, 1 H, 17α-H), 3.60 (d, J=20.1 Hz, 1 H), 3.28 (d, J=20.3, 1 H), 2.68 (dd, J=11.3 Hz, J=8.5 Hz, 1 H), 2.34 (m, 1 H), 2.2–1.20 (m, 16 H), 0.98 (s, 9 H), 0.88 (s, 9 H), 0.78 (s, 3 H), 0.13 (s, 6 H), 0.05 (s, 6 H); CIMS (isobutane) m/z (rel intensity) 573 (MH+, 100). Anal. Calcd for C$_{33}$H$_{56}$O$_4$Si$_2$: C, 69.18; H, 9.85. Found: C, 68.96; H, 9.91.

B-Homo-3,17β-dihydroxy-2-ethoxyestra-1,3,5(10)-triene-7-one (9). Under nitrogen, a mixture of 8 (3.42 g, 5.97 mmol) and a 1.0 M solution of tetrabutylammonium fluoride in THF (50 ml, 50 mmol) was stirred at room temperature for 6 hr. The reaction mixture was poured into an ice-cold sodium bicarbonate solution (200 ml) and then extracted with ethyl acetate (3×100 ml). The ethyl acetate was washed with brine (2×100 ml), dried over sodium sulfate, and evaporated to dryness. Chromatography of the residue (silica gel 230–400 mesh, ethyl acetate:hexane 1:1 by volume) gave the compound 9 as white crystals (1.8 g, 87.4%): mp 210–212° C.; IR (KBr, cm$^{-1}$) 3403 (br., OH), 2970, 2855, 1688, 1582, 1510; $^1$H NMR (CDCl$_3$+DMSO-d$_6$) 6.82 (s, 1 H), 6.69 (s, 1 H), 4.14 (q, J=7.0 Hz, 2 H), 3.69 (t, J=8.5 Hz, 1 H), 3.62 (d, J=20.1 Hz, 1H), 3.32 (d, J=19.8, 1 H), 2.68 (dd, J=11.3 Hz, J=8.5 Hz, 1 H), 2.34–1.20 (m, 16 H), 0.88 (s, 3 H, CH3); CIMS (isobutane) m/z (rel intensity) 345 (MH+, 100). Anal. Calcd for C$_{21}$H$_{28}$O$_4$: C, 73.23; H, 8.19. Found: C, 73.15; H, 7.97.

B-Homo-2-ethoxy-3,17β-dihydroxyestra-1,3,5(10)-triene-7-one toluenesulfonyl-hydrazone (10). Under nitrogen and at room temperature, a mixture of compound 9 (1.73 g, 5.02 mmol) and p-toluenesulfonylhydrazine (4.67 g, 25.1 mmol) in methanol (100 ml) was stirred for 24 hr. The resultant mixture was filtered and the solid washed with cold methanol to afford tosylhydrazone 10 as white crystals (2.48 g, 96.5%). The analytical sample was recrystallized from methanol: mp 179–181° C.; IR (KBr, cm$^{-1}$) 3428 (br., OH, NH), 2922, 1624, 1594, 151 ; $^1$H NMR (CDCl$_3$) δ7.88 (d, J=8.0 Hz, 2 H), 7.34 (d, J=8.0 Hz, 2 H), 7.33 (s, 1 H, NH), 6.71 (s, 1 H), 6.68 (s, 1 H), 5.55 (s, 1 H, OH), 4.11 (q, J=7.0 Hz, 2 H), 3.58 (d, J=19.1 Hz, 2 H), 3.39 (s, 1 H, OH), 3.45 (t, J=8.5, 1 H), 3.15 (d, J=19.1 Hz, 1 H), 2.17–0.99 (m, 16 H), 0.78 (s, 3 H, CH3); CIMS (isobutane) m/z (rel intensity) 360 (MH+, 100), 342 (51). Anal. Calcd. for C$_{21}$H$_{29}$O$_4$N.1/6H2O: C, 69.65; H, 8.16; N, 3.86. Found: C, 69.81; H, 8.06; N, 3.89.

B-Homo-2-ethoxy-3.17β-estradiol (11). Under argon, a solution of 10 (2.27 g, 4.43 mmol) in anhydrous chloroform (150 ml) was cooled to 0° C. and then catecholborane (44.3 ml, 1.0 M solution in THF, 44.3 mmol) was added dropwise at the same temperature. The resultant mixture was stirred for 10 hr, after that sodium acetate trihydrate (12.06 g, 88.62 mmol) was added in portions. The mixture was allowed to warm to room temperature over 30 min and then heated under reflux for 6 hr. The reaction mixture was cooled to room temperature and filtered. The solid material was washed with chloroform (100 ml) and the combined filtrates were evaporated under reduced pressure to dryness. The remaining oil was purified by chromatography on a silica gel column with ethyl acetate:hexane 1:3 by volume. The product was crystallized from ethyl acetate/hexane to give the title compound 11 as white crystals (1.17 g, 80.1%): mp 86–88° C.; IR (KBr, cm$^{-1}$) 3490 (OH), 3259 (OH), 2925, 2861, 1607, 1511; $^1$H NMR (CDCl$_3$+DMSO-d$_6$) δ6.81 (s, 1 H), 6.67 (s, 1 H), 5.46 (s, 1 H, OH), 4.11 (dq, J=3.3 Hz, J=7.0 Hz, 2 H), 3.74 (t, J=8.2 Hz, 1 H), 2.86 (d,t, J=14.6 Hz, J=7.3, 1H), 2.64–2.47 (m, 2 H), 2.14–1.22 (m, 18 H) 0.83 (s, 3 H, CH$_3$); CIMS (isobutane) m/z (rel intensity) 330 (M+, 100). Anal. Calcd for C$_{21}$H$_{30}$O$_3$: C, 76.33; H, 9.15. Found: C, 76.54; H, 9.44.

B-Homo-3,17β-diacetoxy-2-ethoxyestra-1,3,5(10)-triene (12). Acetic anhydride (6 ml, 63 mmol) was added under argon at room temperature to a solution of diol 11 (1.14 g, 3.45 mmol) in anhydrous pyridine (12 ml). The resulting mixture was stirred at room temperature for 24 hr and then poured into ice/water mixture (100 g). The compound was extracted with ethyl acetate (3×70 ml). The organic layers were washed with water (100 ml), aqueous sodium bicarbonate (2×100 ml) and brine (2×100 ml), dried over sodium sulfate and evaporated to dryness. Chromatography of the residue on silica gel (230–400 mesh) using ethyl acetate:hexane 1:1 by volume gave the compound 12 (1.43 g, 100%), which was crystallized from ethyl acetate/hexane to afford white crystals: mp 98–100° C.; IR (KBr, cm$^{-1}$) 2928, 2870, 1768 (3-C=O), 1735 (17-C=O), 1510; $^1$H NMR (CDCl$_3$) δ6.89 (s. 1 H), 6.75 (s, 1 H), 4.70 (t, J=8.7 Hz, 1 H, 17α-H), 4.06 (dq, J=3.3 Hz, J=7.0 Hz, 2 H), 2.89 (dt, J=14.6 Hz, J=7.3, 1 H), 2.64–2.52 (m, 2 H), 2.29 (s, 3 H, COCH$_3$), 2.07 (s, 3 H, COCH$_3$), 2.23–1.26 (m, 18 H), 0.88 (s, 3 H, CH$_3$); CIMS (isobutane) m/z (rel intensity) 415 (MH+, 48), 355 (100). Anal. Calcd for C$_{25}$H$_{34}$O$_5$: C, 72.43; H, 8.27. Found: C, 72.79; H, 8.49.

B-Homo-3,17β-diacetoxy-2-ethoxyestra-1,3,5(10)-triene-6-one (13). A solution of chromium trioxide (1.34 g, 13.4 mmol) in 90% glacial acetic acid (13 ml) was added dropwise over a period of 20 min at 13–15° C. to a well-stirred solution of compound 12 (1.29 g, 3.11 mmol) in glacial acetic acid (35 ml), the resulting mixture was then stirred at 13–15° C. for 15 min. The mixture was poured into ice-water mixture (300 g) and extracted with ethyl acetate (3×200 ml). The combined organic layers were washed with brine (2×100 ml), aqueous sodium bicarbonate (2×100 ml) and brine (2×100 ml), dried over sodium sulfate and evaporated to dryness. Chromatography of the residue on a silica gel column using 20% ethyl acetate in hexane gave ketone 13 (925 mg, 69.3%), which was crystallized from ethyl acetate/hexane to afford white crystals: mp 178–180° C.; IR (KBr, cm$^{-1}$) 2935, 2865, 1774 (3-C=O), 1728 (17-C=O), 1669 (6-C=O), 1500; $^1$H NMR (CDCl$_3$) δ7.36 (s, 1 H), 6.84 (s, 1 H), 4.72 (t, J=8.3 Hz, 1 H, 17α-H), 4.13 (q, J=7.0 Hz, 2 H), 2.64–2.52 (m, 3 H), 2.29 (s, 3 H, COCH$_3$), 2.07 (s, 3 H, COCH$_3$), 2.23–1.26 (m, 18 H), 0.94 (s, 3 H, CH$_3$); CIMS (isobutane) m/z (rel intensity) 429 (MH+, 49), 341 (100). Anal. Calcd for C$_{25}$H$_{32}$O$_6$: C, 70.07; H, 7.53. Found: C, 70.42; H, 7.75.

B-Homo-2-ethoxy-6-oxoestra-1,3,5(10)-trien-3,17β-diol (14). Under nitrogen, a suspension of compound 13 (0.95 g, 2.2 mmol) in anhydrous methanol (10 ml) was cooled to −5–0° C. and then a 20% solution of potassium hydroxide in methanol (10 ml, KOH 1 g, 17.8 mmol) was added dropwise. The resulting mixture was allowed to warn to room temperature and stirred for 3.5 hr. The mixture was cooled to 0° C. and then neutralized with 3 N HCl to pH 5, and allowed to precipitate in a refrigerator overnight. The resultant mixture was filtered to afford 14 as a white solid (725 mg, 95%), which was recrystallized from methanol to afford an analytical sample: mp 198–200° C.; IR (KBr, cm$^{-1}$) 3497 (OH), 3281 (OH), 2935, 2882, 1650 (6-C=O), 1608, 1508; $^1$H NMR (CDCl$_3$) δ7.22 (s, 1 H, 4-ArH), 6.76 (s, 1 H, 1-ArH), 4.19 (q, J=7 Hz, 2 H, 2-CH$_2$—), 3.78 (t, J=8.5 Hz, 1 H, 17α-H), 2.54 (m, 3 H), 2.15–1.21 (m, 18 H), 0.90 (s, 3 H, 18-CH$_3$); CIMS (isobutane) m/z (rel intensity) 345 (MH+, 100). Anal. Calcd for C$_{21}$H$_{28}$O$_4$: C, 73.23; H, 8.19. Found: C, 73.40; H, 8.43.

B-Homo-3,17β-dihydroxy-2-ethoxyestra-1,3,5(10)trien-7-one (9); B-Homo-3,17β-dihydroxy-2-ethoxyestra-1,3,5 (10)trien-6-one (14). A solution of trimethylsilyldiazomethane (4.83 ml, 2 M in hexane, 9.7 mmol) was added dropwise to a solution of ketone 5 (1 g, 2.41 mmol) in dichloromethane (40 ml) containing BF$_3$.Et$_2$O (1.5 ml, 12.2 mmol) at −20° C. The reaction mixture was maintained at the same temperature for 3 hr and poured over ice/water (50 ml). The organic layer was dried (Na$_2$SO$_4$) and the solvent was removed. The residue was then dissolved in diethyl ether (40 ml), silica gel (20 g) and 6 M HCl (1 ml) were added and the reaction mixture was stirred at room temperature for 4 hr. Usual workup of the reaction mixture gave a sticky residue which was dissolved in anhydrous methanol (30 ml). A 20% solution of KOH in methanol (15 ml) was slowly added and the reaction mixture was stirred at room temperature for additional 4 hr. It was then neutralized with 6 M HCl and the solvent was removed. Extraction of the crude product with organic solvent followed by column chromatography(silica gel: 230–420 mesh, 1:2 ethyl acetate-hexane) gave compound 14 (0.2 g, 24%) and compound 9 (0.26 g, 31.3%). The IR and NMR spectra of these compounds were identical with those of the samples described above.

B-Homo-2-ethoxy-3,17β-dihydroxyestra-1,3,5(10)-trien-7-one hydrazone (15). Under nitrogen and at room temperature, compound 9 (60 mg, 0.17 mmol) was dissolved in anhydrous pyridine (5 ml) and then hydroxylamine hydrochloride (240 mg, 3.48 mmol) was added. The reaction mixture was stirred at room temperature for 40 hr. The pyridine was removed under reduced pressure at 30–35° C. The residue was dissolved in ethyl acetate (50 ml) and water (30 ml) and the ethyl acetate was washed with brine (2×20 ml), dried over sodium sulfate, and evaporated to dryness. Chromatography of the residue (silica gel 230–400 mesh, ethyl acetate:hexane 1.25:1 by volume) gave the compound 16 as off-white crystals (50.3 mg, 80.3%): mp 236–238° C.; IR (KBr, cm$^{-1}$) 3292 (br. OH, N=OH), 2930, 1737 (w, C=N), 1592, 1510; $^1$H NMR (CDCl$_3$+DMSO-d$_6$) δ9.88 (s, 1 H, C=NOH), 7.03 (s, 1 H, OH), 6.77 (s, 1 H,), 6.71 (s, 1 H), 4.12 (q, J=7.0 Hz, 2 H), 3.86 (d, J=20.1 Hz, 1 H), 3.68 (t, J=8.5 Hz, 1 H), 3.43 (d, J=19.8, 1 H), 2.20–1.10 (m, 16 H), 0.84 (s, 3 H); CIMS (isobutane) m/z (rel intensity) 514 (MH+, 1.10). Anal. Calcd for C$_{28}$H$_{36}$O$_5$N$_2$S: C, 65.6; H, 7.08; N, 5.46. Found: C, 65.80; H, 7.33; N, 5.35.

B-Homo-2-ethoxyestra-1,3,5(10),6-tetraene-3,17,β-diol (16). A solution of methyllithium in THF/cumene (1.0 M, 2 ml, 2.0 mmol) was added dropwise to a stirred solution of tosylhydrazone 10 (75 mg, 0.15 mmol) in THF (10 ml) under argon at 0° C. The reaction mixture was allowed to warm to room temperature after 2 hr. After stirring a further 20 hr at room temperature, the reaction mixture was poured into ice (50 g) and acidified with 6 N HCl. The resultant mixture was extracted with ethyl acetate (3×30 ml) and the organic extracts were washed with saturated sodium sulfate (30 ml) and brine (2×30 ml), combined and dried over sodium sulfate, and evaporated to dryness. Chromatography of the residue on silica gel (230–400 mesh) using ethyl acetate:hexane 2:5 by volume gave the compound 16 (26 mg, 54%), which was crystallized from ethyl acetate/hexane to afford white crystals: mp 167–168° C.; IR (KBr, cm$^{-1}$) 3503 (OH), 3231 (OH), 2930, 1603 (w, C=C), 1510; $^1$H NMR (CDCl$_3$) δ6.82 (s, 1 H), 6.70 (s, 1 H), 6.54 (d, J=10.1 Hz, 1 H), 6.06 (m, 1 H), 5.51 (s, OH, 1 H), 4.15 (q, J=7.0 Hz, 2 H), 3.74 (t, J=8.7 Hz, 1 H, 17α-H), 2.12–1.21 (m, 14 H), 0.84 (s, 3 H, CH$_3$); CIMS (isobutane) m/z (rel intensity) 329 (MH+, 100), 311 (52). Anal. Calcd for C$_{21}$H$_{28}$O$_3$.1/4H2O: C, 75.58; H, 8.84. Found: C, 75.62; H, 8.65.

B-Homo-17β-acetoxy-2-ethoxy-3-hydroxyestra-1,3,5 (10)-trien-6-one (18). Under nitrogen, a solution of compound 13 (65 mg, 0.15 mmol) in methanol (10 ml) was deoxygenated by bubbling through it a slow stream of nitrogen for 30 min. A similarly deoxygenated solution of KHCO$_3$ (152 mg, 1.52 mmol) in water (1 ml) was added and the reaction mixture was stirred and heated at 65° C. (outer bath) for 1.5 hr. The reaction mixture was cooled to room temperature and then neutralized to pH=6 with 6 N HCl. The solvents were removed under reduced pressure and the residue was dissolved in a mixture of ethyl acetate (50 ml) and water (50 ml). The ethyl acetate layer was separated, dried over sodium sulfate and evaporated to dryness. Chromatography of the residue (silica gel 230–400 mesh, ethyl acetate:hexane 1:2 by volume) gave the monoacetate 18 (56 mg, 95%), which was recrystallized from ethyl acetate/hexane to afford white crystals: mp 240–242° C.; IR (KBr, cm$^{-1}$) 3385 (OH), 2941, 1721 (17-C=O), 1663 (6-C=O), 1614, 1511; $^1$H NMR (CDCl$_3$) δ7.22 (s, 1 H, 4-ArH), 6.75 (s, 1 H, 1-ArH), 5.54 (s, 1 H, 3-ArOH), 4.72 (t, J=8.5 Hz, 1 H, 17α-H), 4.19 (q, J=7 Hz, 2 H, 2-CH$_2$—), 2.58 (m, 3 H), 2,55 (m, 1 H), 2.08 (s, 3 H, 3-CH$_3$CO), 1.94–1.27 (m, 11 H), 0.88 (s, 3 H, 18-CH$_3$) CIMS (isobutane) m/z (rel intensity) 387 (MH+, 100); Anal. Calcd for C$_{23}$H$_{30}$O$_5$: C, 71.48; H, 7.82. Found C, 71.22; H, 7.86.

B-Homo-3-Acetoxy-2-ethoxy-17β-hydroxyestra-1,3,5 (10)-trien-6-one(19). Under argon and at room temperature, diol 14 (60 mg, 0.17 mmol) was dissolved in THF (4 ml) and 1 N NaOH (0.19 ml, 0.19 mmol) was added to the solution. After stirring for 20 min, a solution of 1-acetyl-1 H-1,2,3-triazolo[4,5-b]pyridine (31 mg, 0.19 mmol) in THF (2 ml) was added dropwise to the above reaction mixture. The reaction mixture was stirred at room temperature for 1.5 hr. The reaction mixture was poured into ice (20 g) and neutralized to pH 6 with 2 N HCl, and then extracted with ethyl acetate (2×30 ml). The ethyl acetate layers were combined, dried over sodium sulfate and evaporated to dryness. Chromatography of the residue (silica gel 230–400 mesh, ethyl acetate:hexane =1:3 by volume) gave compound 19 (61 mg, 90%), which was obtained as a white foam by evaporation of a hexane solution under high vacuum at 40–50° C.; IR (KBr, cm$^{-1}$) 3449 (br. OH), 2933, 1766 (3-C=O), 1669 (6-C=O), 1605, 1502; $^1$H NMR (CDCl$_3$) δ7.36 (s, 1 H, 4-Ar—H), 6.86 (s, 1 H, 1-Ar—H), 4.14 (q, J=7 Hz, 2 H, 2-CH$_2$—), 3.78 (t, J=8.5 Hz, 1 H, 17α-H), 2.59 (m, 3 H), 2.55 (m, 1H), 2.30 (s, 3 H, 17-CH$_3$CO), 2.15–1.27 (m, 11 H), 0.89 (s, 3 H, 18-CH$_3$); CIMS (isobutane) m/z (rel intensity) 387 (MH+, 100); Anal. Calcd for C$_{23}$H$_{30}$O$_5$: C, 71.48; H, 7.82. Found C, 71.60; H, 8.16.

B-Homo-2-ethoxy-6-methoximinoestra-1,3,5(10)-trien-3,17β-diol (20). To a solution of diacetate 13 (76 mg, 0.21 mmol) in pyridine (10 ml) was added methoxylamine hydrochloride (354 mg, 4.23 mmol) in one portion under nitrogen. The resulting mixture was heated at 100° C. for 3 hr and then cooled to about 50° C. The pyridine was removed under reduced pressure. The residue was dissolved in a mixture of ethyl acetate (50 ml) and water. The ethyl acetate solution was separated and then washed with brine (2×30 ml), dried over sodium sulfate, and evaporated to dryness. Chromatography of the residue (silica gel 230–400 mesh, ethyl acetate:hexane 3:5 by volume) gave compound 20 (78 mg, 94%), which was crystallized from ethyl acetate/hexane to afford white crystals: mp 181–183° C.; IR (KBr, cm$^{-1}$) 3511 (OH), 3318 (OH), 2972, 2987,1618, 1576, 1508; $^1$H NMR (CDCl$_3$) δ7.03 (s, 1 H, 4-ArH), 6.74 (s, 1 H, 1-ArH), 5.53 (s, 1 H, 3-ArOH), 4.17 (q, J=7 Hz, 2 H, 2-CH$_2$—), 4.14 (s, 3 H, -OCH$_3$), 3.78 (t, J=8.5 Hz, 1 H, 17α-H), 2.58 (m, 2 H), 1.94 (m, 3 H), 1.78–1.27 (m, 15 H), 0.88 (s, 3 H, 18-CH3); CIMS (isobutane) m/z (rel intensity) 374 (MH+, 100). Anal. Calcd for C$_{22}$H$_{31}$O$_4$N: C, 70.75; H, 8.37; N 3.75. Found: C, 70.75; H, 8.41; N 3.61.

B-Homo-3,17β-diacetoxy-2-ethoxy-6-methoximinoestra-1.3.5(10)-triene (21). Acetic anhydride (0.6 ml, 6.3 mmol) was added under argon at room temperature to a solution of compound 20 (46 mg, 0.12 mmol) in anhydrous pyridine (3 ml). The resulting mixture was stirred at room temperature for 20 hr and then poured into ice/water mixture (50 g). The compound was extracted with ethyl acetate (3×40 ml). The organic layers were washed with sodium bicarbonate (50 ml) and brine (50 ml), dried over sodium sulfate and evaporated to dryness. Chromatography of the residue on a silica gel (230–400 mesh) column using ethyl acetate:hexane 1:5 by volume gave the compound 27 (51 mg, 90%), which was dried under high vacuum at 40–50° C. to give the title compound 21 as a stable white foam: IR (KBr, cm$^{-1}$) 2934, 1770 (3-C=O), 1734 (17-C=O), 1614, 1500; $^1$H MR (CDCl$_3$) δ7.12 (s, 1 H, 4-ArH), 6.81 (s, 1 H, 1-ArH), 4.72 (t, J=8.5 Hz, 1 H, 17α-H), 4.08 (q, J=7 Hz, 2 H, 2-CH$_2$—), 3.96 (s, 3 H, —OCH$_3$), 2.57 (m, 2 H), 2.38 (s, 3 H, 3-CH$_3$CO), 2.06 (s, 3 H, 17-CH$_3$CO), 2.32–1.26 (m, 14 H), 0.90 (s, 3 H, 18-CH$_3$); CIMS (isobutane) m/z (rel intensity) 458 (MH+, 100). Anal. Calcd for C$_{26}$H$_{35}$O$_6$N: C, 68.25; H, 7.71; N 3.06. Found C, 68.45; H, 7.87; N 2.79.

B-Homo-2-ethoxy-6-hydroximinoestra-1,3,5(10)-trien-3,17β-diol (22). Under nitrogen and at room temperature, compound 14 (200 mg, 0.58 mmol) was dissolved in anhydrous pyridine (10 ml) and then hydroxylamine hydrochloride (807 mg, 11.6 mmol) was added. The reaction mixture was stirred at room temperature for 20 hr. The pyridine was removed under reduced pressure at 30–35° C. and the residue was dissolved in a mixture of ethyl acetate (50 ml) and water (30 ml). The ethyl acetate layer was separated and washed with brine (2×20 ml), dried over sodium sulfate, and evaporated to dryness. Chromatography of the residue ( silica gel 230–400 mesh, ethyl acetate : hexane 5:4 by volume) gave the title compound 22 (198 mg, 95%), which was recrystallized from ethyl acetate to afford white crystals: mp 226–228° C.; mg, 80.3%); IR (KBr, cm$^{-1}$) 3452 (OH), 3160 (OH), 3039, 2932, 2897, 1722 (w, 6-C=N), 1599, 1150; $^1$H NMR (CDCl$_3$+DMSO-d$_6$) δ9.73 (s, 1 H, C=NOH), 7.34 (s, 1 H), 6.73 (s, 1 H), 6.17 (s, 1 H, OH), 4.15 (q, J=7.0 Hz, 2 H), 3.86 (d, J=20.1 Hz, 1 H), 3.73 (t, J=8.5 Hz, 1 H), 2.63–1.17 (m, 19 H), 0.86 (s, 3 H); CIMS (isobutane) m/z (rel intensity) 360 (MH+, 100). Anal. Calcd for C$_{21}$H$_{29}$O$_4$N: C, 70.17; H, 8.13; N, 3.90. Found: C, 70.16; H, 8.45; N, 3.69.

B-Homo-6β-actamido-3,17α-diacetoxy-2-ethoxyestra-1,3,5(10)-triene (23).

To a solution of compound 14 (270 mg, 0.78 mmol) and ammonium acetate (4.0 g, 51.9 mmol ) in anhydrous methanol (20 ml) was added sodium cyanoborohydride (493 mg, 7.8 mmol) at room temperature under argon. The reaction mixture was stirred at room temperature for 30 min and then refluxed at 65–70° C. for 48 hr. The mixture was cooled to about 40° C. and then the solvent was removed under reduced pressure. The residue w as treated with saturated NaHCO$_3$ (50 ml) and ethyl acetate (3×50 ml). The ethyl acetate layers were washed with brine (2×30 ml), combined and dried over sodium sulfate, and evaporated to dryness. The residue was dissolved in anhydrous pyridine (10 ml) and acetic anhydride (4 ml) was added, and the resultant mixture was stirred at room temperature under argon for 14 hr. The pyridine and excess acetic anhydride were removed under reduced pressure at 40–45 ° C. and the residue dissolved in ethyl acetate (100 ml). The ethyl acetate solution was washed with saturated NaHCO$_3$ (50 ml) and brine (50 ml), dried over sodium sulfate, and evaporated to dryness. Chromatography of the residue on silica gel (230–400 mesh) using ethyl acetate:hexane 7:2 by volume gave the compound 23 (99 mg, 27%), which was dried under high vacuum at 40–50° C. to give stable white foam: IR (KBr, cm$^{-1}$) 3313 (6-NH), 2935; 1765 (3-C=O) 1733 (17-C=O), 1655 (6-NC=O), 1510; $^1$H NMR (CDCl$_3$) δ6.95 (s, 1 H, 4-ArH), 6.85 (s, 1 H, 1 H-ArH), 5.80 (d, J$_{NH-6}$=7.2 Hz, 6β-CNH, 1 H), 5.13 (ddd, J$_{NH-6}$=7.2 Hz, J$_{6-7}$=11.7 and 6.4 Hz, 6α-CH), 4.73 (t, J=8.5 Hz, 1 H, 17α-H), 4.08 (qd, J=7.1 Hz, J=1.5 Hz, 2 H, 2-CH$_2$—), 2.56 (m, 1 H), 2.28 (s, 3 H, 3-CH$_3$CO), 2.07 (s, 3 H, 17-CH$_3$CO), 1.95 (s, 6-NCOCH$_3$, 3 H), 2.36–1.26 (m, 14 H), 0.90 (s, 3 H, 18-CH$_3$); CIMS (isobutane) m/z (rel intensity) 472 (MH+, 100). Anal. Calcd for C$_{27}$H$_{37}$O$_6$N: C, 68.77; H, 7.91; N, 2.97. Found: C, 68.87; H, 8.15; N, 2.87.

B-Homo-6β-actamido-3,17β-diacetoxy-2-ethoxyestra-1,3,5(10)-triene (24). The chromatographic purification of 23 described above also provided compound 24 as a white foam (180 mg, 48%): IR (KBr, cm$^{-1}$) 3313 (6-NH), 2935; 1765 (3-C=O), 1734 (17-C=O), 1655 (NC=O), 1510; $^1$H NMR (CDCl$_3$) δ6.88 (s, 1 H, 4-ArH), 6.78 (s, 1 H 1-ArH), 5.68 (d, J$_{NH-6}$=8.5 Hz, 6α-CNH, 1 H), 5.40 (ddd, J$_{NH-6}$=8.5 Hz, J$_{6-7}$=11.7 and 6.4 Hz, 6β-CH), 4.69 (t, J=8.5 Hz, 1 H, 17α-H), 4.08 (qd, J=7 Hz, J=1.5 Hz, 2 H, 2-CH$_2$—), 3.96 (s, 3 H, —OCH$_3$), 2.52 (m, 1 H), 2.30 (s, 3 H, 3-CH$_3$CO), 2.10 (s, 3 H, 17-CH$_3$CO), 2.07 (s, 6-NCOCH$_3$, 3 H), 2.36–1.26 (m, 14 H), 0.88 (s, 3 H, 18-CH$_3$); CIMS (isobutane) m/z (rel intensity) 472 (MH+, 100). Anal. Calcd for C$_{27}$H$_{37}$O$_6$N: C, 68.77; H, 7.91; N, 2.97. Found: C, 68.85; H, 8.15; N, 2.90.

B-Homo-6α-acetamido-2-ethoxyestra-1,3,5(10)-trien-3,17β-diol (25). A solution of compound 23 (75 mg, 0.16 mmol) in methanol (14 ml) was deoxygenated by bubbling through it a slow stream of nitrogen for 30 min. A similarly deoxygenated 1 M solution of sodium hydroxide in water (1.6 ml, 16 mmol) was added and the mixture stirred at room temperature for 5 hr. The reaction mixture was neutralized with acetic acid to pH 6, and the solvents were removed under reduced pressure. The residue was dissolved in a mixture of ethyl acetate (60 ml) and saturated sodium bicarbonate (50 ml). The organic layer was separated and then washed with brine (2×30 ml), dried over sodium sulfate, and evaporated to dryness. Chromatography of the residue on a silica gel column using methylene chloride:acetone 2:1 by volume gave the title compound 25 (42 mg, 68%), which solidified from an acetone-hexane-methylene chloride mixture to afford a white solid: mp 196–198° C.; IR (KBr, cm$^{-1}$) 3328 (OH), 3313 (6-NH), 2937; 1650 (6-NC=O), 1512; 1 H NMR (CDCl$_3$) δ6.84 (s, 1 H, 4-ArH), 6.77 (s, 1 H, 1-ArH), 5.73 (d, J$_{NH}$-6=7.2 Hz, 6β-CNH, 1 H), 5.57 (s, OH, 1H), 5.08 (ddd, J$_{NH-6}$=7.2 Hz, J$_{6-7}$=11.7 and 6.4 Hz, 6α-CH), 4.08 (qd, J=7 Hz, J=1.5 Hz, 2 H, 2-CH2—), 3.75 (t, J=8.5 Hz, 1 H, 17α-H), 2.50 (m, 1 H), 2.33 (m, 1 H), 1.95 (s, 6-NCOCH3, 3 H), 2.18–1.26 (m, 17 H), 0.85 (s, 3 H, 18-CH3); CIMS (isobutane) m/z (rel intensity) 388

(MH+, 100). Anal. Calcd for ($C_{23}H_{33}O_4N.2/3CH_3COCH_3$): C, 70.44; H, 8.75; N 3.28. Found: C, 70.60; H, 9.14; N, 3.59.

B-Homo-6β-acetamido-2-ethoxyestra-1,3,5(10)-trien-3,17β-diol (26). Compound 24 (178 mg, 0.38 mmol) was treated by the method described above for the preparation of 25 to give 26 (98 mg, 67%), which solidified from acetone-hexane-methylene chloride to afford a white solid: mp>162° C. (dec.); IR (KBr, cm$^{-1}$) 3314 (OH, 6-NH), 2927; 1658 (6-NC=O), 1506; $^1$H NMR (CDCl$_3$) δ6.78 (s, 1 H, 4-ArH), 6.72 (s, 1 H, 1-ArH), 5.71 (d, $J_{NH}$-6=8.8 Hz, 6α-CNH, 1 H), 5.61 (s, OH, 1 H), 5.38 (ddd, $J_{NH}$-6=8.8 Hz, $J_{6-7}$=11.7 and 6.4 Hz, 6β-CH), 4.11 (qd, J=7.1 Hz, J=1.5 Hz, 2 H, 2-CH$_2$—), 3.75 (t, J=8.5 hz, 1 H, 17α-H), 2.48 (m, 1 H), 2.10 (s, 6-NCOCH$_3$, 3 H), 2.18–1.26 (m, 18 H), 0.83 (s, 3 H, 18-CH$_3$); CIMS (isobutane) m/z (rel intensity) 388 (MH+, 100). Anal. Calcd for $C_{23}H_{33}O_4N$: C, 71.29; H, 8.58; N 3.61. Found: C, 71.09; H, 8.85; N, 3.49.

17β-Acetoxy-2-ethoxy-6-hydroximinoestra-1,3,5(10)-triene-3-ol (27). A solution of 3,17,β-diacetoxy-2-ethoxyestra-1,3,5(10)-triene-6-one (5, 800 mg, 1.93 mmol) in pyridine (12 ml) was treated with hydroxylamine hydrochloride (1.07 g, 15.4 mmol). The resulting mixture was stirred and heated at 100° C. for 30 min. The mixture was cooled to room temperature and then poured into ice/water mixture (150 ml). The compound was extracted with ethyl acetate (3×100 ml). The combined organic layers were washed with sodium bicarbonate (100 ml), water (2×100 ml) and brine (2×100 ml), dried over sodium sulfate, and evaporated to dryness. Chromatography of the residue on silica gel using 30% ethyl acetate in hexane gave the title compound (763 mg, 89%), which was crystallized from ethyl acetate/hexane to afford title compound 27 as yellowish crystals: mp 226–227° C. $^1$H NMR (CDCl$_3$) δ7.55 (s, 1 H). 6.78 (s, 1 H), 4.75 (t, J=8.5 Hz, 1 H), 4.19 (q, J=6.9 Hz, 2 H), 3.15 (dd, J=4.3 and 12 Hz, 1 H), 1.2–2.40 (m, 18 H), 0.85 (s, 3 H); CIMS (isobutane) m/z (rel intensity) 388 (MH+, 100), 372 (MH—H$_2$O, 10), 328 (75); Anal. Calcd for $C_{22}H_{29}O_5N$: C, 68.20; H, 7.54; N, 3.61. Found: C, 68.04; H, 7.62; N, 3.54.

B-Homo-6-aza-2-ethoxy-3,17β-dihydroxyestra-1,3,5(10)-trien-7-one (29). To a solution of 27 (700 mg, 1.63 mmol) in pyridine (10 ml) was added p-toluenesulfonyl chloride (686 mg, 3.6 mmol). The resulting mixture was stirred at room temperature for 2 hr, and the pyridine was then removed in vacuo at ambient temperature. The residue, containing O-toluenesulfonyloxime 28, was dissolved in 40% chloroform in benzene (5 ml) and the material was applied to the top of a basic alumina column (30×3.5 cm). The column was eluted with chloroform/benzene (40–90% chloroform) and then allowed to stand overnight. The column was then eluted with methanol (200 ml) and then with 80% methanol in water (200 ml). The methanol eluant was collected and evaporated to dryness. Chromatography of the residue on a silica gel column using ethyl acetate gave the title compound 29 (267 mg, 47%), which was crystallized from ethyl acetate to afford white crystals: mp 222–223° C. $^1$H NMR (CDCl$_2$) δ7.31 (br.s., N—H, 1 H). 7.55 (s, 1 H, 4-aromatic CH), 6.78 (s, 1 H, 1-aromatic CH), 4.19 (q, J=6.9 Hz, 2 H, 2-CH$_2$—), 3.75 (t, J=8.5 Hz, 1 H, 17a-H), 2.41 (m, 2 H, 7-CH$_2$), 1.43 (t, J=7 Hz, 3 H, 2-CH$_3$), 0.82 (s, 3 H, 18-CH$_3$); CIMS (isobutane) m/z (rel intensity) 346 (MH$^+$, 100), 328 (MH—H$_2$O, 20); Anal. Calcd for $C_{20}H_{27}O_4N.1/3 H_2O$: C, 68.35; H, 7.93; N, 3.98. Found: C, 68.25; H, 8.03 N, 3.82.

B-Homo-6-aza-2-ethoxyestra-1,3,5(10)-triene-3,17β-diol (30). A solution of borane in THF (1.0 M, 5.6 ml, 5.6 mmol) was added dropwise by syringe to a solution of the lactam 29 (97.8 mg, 0.28 mmol) in THF (5 ml) under argon at room temperature, and the resulting solution was stirred for 6 hr and then at gentle reflux for 4 hr. The mixture was cooled and 6 N hydrochloric acid (2 ml) was added slowly through a pipette. The solvent was removed under reduced pressure and the residue was dissolved in ethyl acetate (60 ml). The ethyl acetate solution was washed with sodium bicarbonate (30 ml) and brine (2×20 ml), dried over sodium sulfate and evaporated to dryness. Chromatography of the residue on silica gel using 50% ethyl acetate in methylene chloride gave the title compound 30 (85 mg, 90%), which formed a stable white foam when a methylene chloride solution was evaporated under reduced pressure. $^1$H NMR (CDCl$_3$) δ6.80 (s, 1 H), 6.28 (s, 1 H), 4.05 (q, J=6.9 Hz, 2 H), 3.75 (t, J=8.5 Hz, 1 H), 3.30 (t, J=6.9 Hz, 1 H), 2.82 (t, J=6.9 Hz, 1 H), 2.55 (dt, J=8.5 Hz, J=2 Hz, 1 HH, 9a-H), 1.2 –2.20 (m, 18 H), 0.78 (s, 1 H); CIMS (isobutane) m/z (rel intensity) 332 (MH$^+$, 100), 314 (MH—H$_2$O, 60); Anal. Calcd for $C_{20}H_{29}O_3N.1/4 H_2O$: C, 71.50; H, 8.85; N, 4.14. Found: C, 71.64; H, 8.90; N, 4.29.

B-Homo-6-acetyl-6-aza-3,17β-diacetoxy-2-ethoxyestra-1,3,5(10)-triene (31). Under nitrogen, acetic anhydride (1.83 g, 1.7 ml, 17.65 mmol) was added to a solution of B-homo-6-aza-2-ethoxyestra-1,3,5(10)-triene-3,17β-diol (30, 146 mg, 0.44 mmol) in pyridine (5 ml). The resulting mixture was stirred at room temperature for 24 hr and then poured into ice/water mixture (30 ml). The compounds were extracted with ethyl acetate (3×50 ml) and the organic layers were washed with water (30 ml), saturated sodium bicarbonate (30 ml) and brine (30 ml), dried over sodium sulfate, and evaporated to dryness. Chromatography of the residue on silica gel using 33% ethyl acetate in methylene chloride gave the title compound 31 (169 mg, 84%), which formed a white stable foam when an ethyl acetate/hexane solution was evaporated under reduced pressure. $^1$H NMR (CDCl$_3$) δ6.87 (s, 1 H), 6.78 (s, 1 H), 4.66 (t, J=8.5 Hz, 1 H, 17a-H), 4.09 (q, J=6.9 Hz, 2 H, 2-CH$_2$—), 4.08 (t, J=6.9 Hz, 1 H), 3.09 (m, 1 H), 2.46 (dt, J=8.5 Hz, J=2 Hz, 1 H, 9a-H), 2.4 (s, 3 H, 3-CH$_3$CO), 2.28 (s, 3 H, 17-CH$_3$CO), 1.93 (s, 3 H, N—CH$_3$CO), 0.78 (s, 3 H=6.9 Hz, 1 H); CIMS (isobutane) m/z (rel intensity) 458 (MH$^+$, 100), 398 (35); Anal. Calcd for $C_{26}H_{35}O_6N$: C, 68.25; H, 7.71; N, 3.06. Found: C, 68.36; H, 7.90; N, 3.43.

B-Homo-6-acetyl-6-aza-2-ethoxyestra-1,3,5(10)-triene-3,17β-diol (32). A solution of 31 (150 mg, 0.33 mmol) in methanol (15 ml) was deoxygenated by bubbling through it a slow stream of nitrogen for 30 min. A similarly deoxygenated solution of 1.0 N sodium hydroxide in water (3.2 ml, 3.2 mmol) was added and the mixture stirred at room temperature for 4.5 hr. The reaction mixture was neutralized with acetic acid to pH 6–7 and then the solvents were removed under reduced pressure. The residue was dissolved in ethyl acetate (60 ml) and the organic layer was washed with water (30 ml), sat. sodium bicarbonate (30 ml) and brine (30 ml), dried over sodium sulfate, evaporated to dryness. Chromatography of the residue on silica gel using ethyl acetate gave the title compound 32 (105 mg, 86%), which was crystallized from ethyl acetate/hexane to afford a white crystals: mp 189–191° C.; $^1$H NMR (CDCl$_3$) δ6.77 (s, 1 H), 6.67 (s, 1 H), 4.09 (q, J=6.9 Hz, 2 H, 2-CH$_2$—), 4.08 (t, J=6.9 Hz, 1 H), 3.71 (t, J=8.5 Hz, 1 H, 17a-H), 3.03 (m, 1 H), 2.40 (dt, J=8.5 Hz, J=2 Hz, 1 H, 9a-H), 1.87 (s, 3 H. CH$_3$CON), 0.78 (s, 1 H); CIMS (isobutane) m/z (rel intensity) 374 (MH$^+$, 100); Anal. Calcd for $C_{22}H_{31}O_4N.1/3 H_2O$: C, 69.75; H, 8.41; N, 3.69. Found: C, 69.65; H, 8.25; N, 3.87.

B-Homo-6-aza-2-ethoxy-6-ethylestra-1,3,5(10)-triene-3,17β-diol (33). To a solution of B-homo-6-acetyl-6-aza-2- ethoxyestra-1,3,5(10)-triene-3,17β-diol (32, 90 mg, 0.24 mmol) in THF (5 ml) was added dropwise a solution of borane in THF (1.0 M, 4.8 ml, 4.8 mmol) by syringe under argon. The resulting solution was stirred at room temperature for 4 hr and then at gentle reflux for 4 hr. The mixture was cooled to room temperature and 6 N hydrochloric acid (1 ml) was added slowly through a pipette. The solvent was removed under reduced pressure and the residue was neutralized with saturated sodium bicarbonate solution and then extracted with ethyl acetate (3×30 ml). The ethyl acetate layers were washed with brine (2×30 ml), dried over sodium sulfate and evaporated to dryness. Chromatography of the residue on silica gel using 20% ethyl acetate in methylene chloride gave the title compound 33 (70 mg, 81%), which formed a stable white foam when an ethyl acetate/hexane solution was evaporated under reduced pressure: $^1$H NMR (CDCl$_3$) δ6.68 (s, 1 H), 6.51 (s, 1 H), 4.07 (q, J=6.9 Hz, 2 H), 3.78 (t, J=8.5 Hz, 1 H), 3.38 (td, J=11.5 Hz, J=2.2 Hz, 1 H), 3.2 (qd, J=12.6 Hz, J=7.1 Hz, 1 H) ,2.94 (qd, J=11.7 Hz, J=6.8 Hz, 1 H), 2.75 (td, J=11.5 Hz, J=2.2 Hz, 1 H), 2.55 (dt, J=8.5 Hz, J=2 Hz, 1 H, 9a-H), 1.2–2.20 (m, 18 H), 0.84 (s, 3 H); CIMS (isobutane) m/z (rel intensity) 360 (MH$^+$, 100), 342 (MH—H$_2$O, 50); Anal. Calcd for C$_{22}$H$_{33}$O$_3$N.1/6 H$_2$O: C, 72.96; H, 9.27; N, 3.86. Found: C, 72.97; H, 9.27; N, 3.85.

B-Homo-2-ethoxyestra-3,17β-triol (34). Under argon, sodium borohydride (260 mg, 7 mmol) is added to a solution of 9 (1.73 g, 5.02 mmol) in ethanol. The mixture is stirred overnight at room temperature, then 6 N hydrochloric acid is added dropwise with stirring until the pH is ca. 6. The solvent is removed under reduced pressure and the residue is dissolved in ethyl acetate (1.00 ml). The ethyl acetate solution is washed with sodium bicarbonate (50 ml) and brine (2×25 ml), dried over sodium sulfate, and evaporated to dryness. Chromatography of the residue on silica gel using a gradient of ethyl acetate in methylene chloride gives the title compound 34 as a mixture of C-7 diastereomers.

B-Homo-3,17β-triacetoxy-2-ethoxyestra-1,3,5). Acetic anhydride (6 ml, 63 mmol) is added under argon at room temperature to a solution of triol 34 (1.10 g, 3.18 mmol) in anhydrous pyridine (12 ml). The resulting mixture is stirred at room temperature for 24 hr and then poured into ice/water mixture (100 g). The compound is extracted with ethyl acetate (3×70 ml). The organic layers are washed with water (100 ml), aqueous sodium bicarbonate (2×100 ml) and brine (2×100 ml), dried over sodium sulfate, and evaporated to dryness. Chromatography of the residue on silica gel (230–400 mesh) using ethyl acetate:hexane 1:1 by volume provides the title compound 35 as a mixture of C-7 diastereomers.

B-Homo-2-ethoxyestra-3,6,17β-triol (36). Under argon, sodium borohydride (260 mg, 7 mmol) is added to a solution of 14 (1.73 g, 5.02 mmol) in ethanol. The mixture is stirred overnight at room temperature, then 6 N hydrochloric acid is added dropwise with stirring until the pH is ca. 6. The solvent is removed under reduced pressure and the residue is dissolved in ethyl acetate (100 ml). The ethyl acetate solution is washed with sodium bicarbonate (50 ml) and brine (2×25 ml), dried over sodium sulfate, and evaporated to dryness. Chromatography of the residue on silica gel using a gradient of ethyl acetate in methylene chloride gives the title compound 36 as a mixture of C-6 diastereomers.

B-Homo-3,17β-triacetoxy-2-ethoxyestra-1,3,5(10)-triene (37). Acetic anhydride (6 ml, 63 mmol) is added under argon at room temperature to a solution of triol 36 (1.10 g, 3.18 mmol) in anhydrous pyridine (12 ml). The resulting mixture is stirred at room temperature for 24 hr and then poured into ice/water mixture (100 g). The compound is extracted with ethyl acetate (3×70 ml). The organic layers are washed with water (100 ml), aqueous sodium bicarbonate (2×100 ml) and brine (2×100 ml), dried over sodium sulfate, and evaporated to dryness. Chromatography of the residue on silica gel (230–400 mesh) using ethyl acetate:hexane 1:1 by volume provides the title compound 35 as a mixture of C-6 diastereomers.

Anti-mitotic Activity In Vivo

Anti-angiogenic activity is evaluated in vivo by testing the ability of a compound to inhibit the proliferation of new blood vessel cells (angiogenesis). A suitable assay is the chick embryo chorioallantoic membrane (CAM) assay described by Crum et al., *Science* 230:1375 (1985). See also, U.S. Pat. No. 5,001,116, which is hereby incorporated by reference in its entirety. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the disc, the diameter of that zone is measured. Using this assay, a 100 mg disk of 2-methoxyestradiol is found to inhibit cell mitosis and the growth of new blood vessels after 48 hours.

Alternatively, anti-angiogenic activity can be assayed in vivo by the "mouse corneal micropocket assay" described by Kenyon et al., *Opthalmol. & Visual Sci.*, 76:1625–1632 (1996); see also Klauber et al., *Cancer Res* 57:81–86 (1997).

Tubulin polymerization Inhibition In Vitro

Potential anti-mitotic activity can be screened for by testing the ability of a compound to inhibit tubulin polymerization and microtubule assembly in vitro. Microtubule assembly is followed in a temperature controlled recording spectrophotometer. For details and a discussion, see R. D'Amato et al., *Proc Natl Acad Sci USA*, 91:3964–3968 (1994).

A typical reaction mixture, which will have a final reaction volume of 0.25 μl, contains 1.0 M monosodium glutamate (pH 6.6), 1.0 mg/ml (10 μM) tubulin, 1.0 MM MgCl$_2$, 4% (v/v) dimethylsulfoxide, and a compound to be tested at the desired concentration (typically 0.1 to 100 μM). The reaction mixtures are incubated for 15 min. at 37° C. and then chilled on ice. After addition of 10 μl 12.5 mM GTP (and, optionally, 0.33 mg/ml microtubule-associated proteins, or MAPs) to initiate polymerization, each reaction mixture is transferred to a cuvette at 0° C., and a baseline established. At time zero, the temperature controller of the spectrophotometer is set to a target temperature, typically between 25 and 37° C. Microtubule assembly is monitored by observing an increase in turbidity at 350 nm as the temperature of the reaction mixture rises to the set target temperature.

The presence or absence of MAPs appears to affect the mechanism of polymerization to some extent, since the relative potencies of taxotere and certain compounds of this invention are dependent on the presence of MAPs.

The results are presented in Table 1 as IC$_{50}$ values (μM) for inhibition of tubulin polymerization. Alternatively, inhibition of microtubule assembly can be detected by transmission electron microscopy, as described in U.S. Pat. No. 5,504,074 which is hereby incorporated by reference in its entirety.

In those cases where acceleration of tubulin polymerization is observed, an IC$_{50}$ value for inhibition of polymerization is of course not derivable. Results for such compounds may be presented in the form of turbidimetric curves, e.g. as presented in FIGS. 4 and 5 for representative compounds 13 and 18. The diacetate 13 had paclitaxel-like properties in both glutamate- and MAP-induced assembly reactions, whereas the diol 14 was inactive. Removal of the C-17 O-acetyl group yielded the inactive compound 19, but activity was largely retained upon selective removal of the C-3 O-acetyl group (compound 18). The paclitaxel-like properties of compounds 13 and 18 included more rapid induction of polymer at reduced temperatures (25–26° C.), formation of microtubules stable to disassembly at 0° C., reduction of the tubulin critical concentration, and polymer formation in 0.1 M 4-morpholineethanesulfonate in the absence of MAPs. In contrast to observations with paclitaxel (Grover et al., Biochemistry 34:3927–3934 (1995)), tubulin assembly has not been observed in the absence of GTP with either 13 or 18. Although inhibition of [$^3$H]paclitaxel binding to tubulin polymer by compound 13 is not substantial (maximal inhibition observed was about 20%), it is reproducible, suggesting that the compound binds in or close to the paclitaxel site on tubulin polymers.

Figure 4:
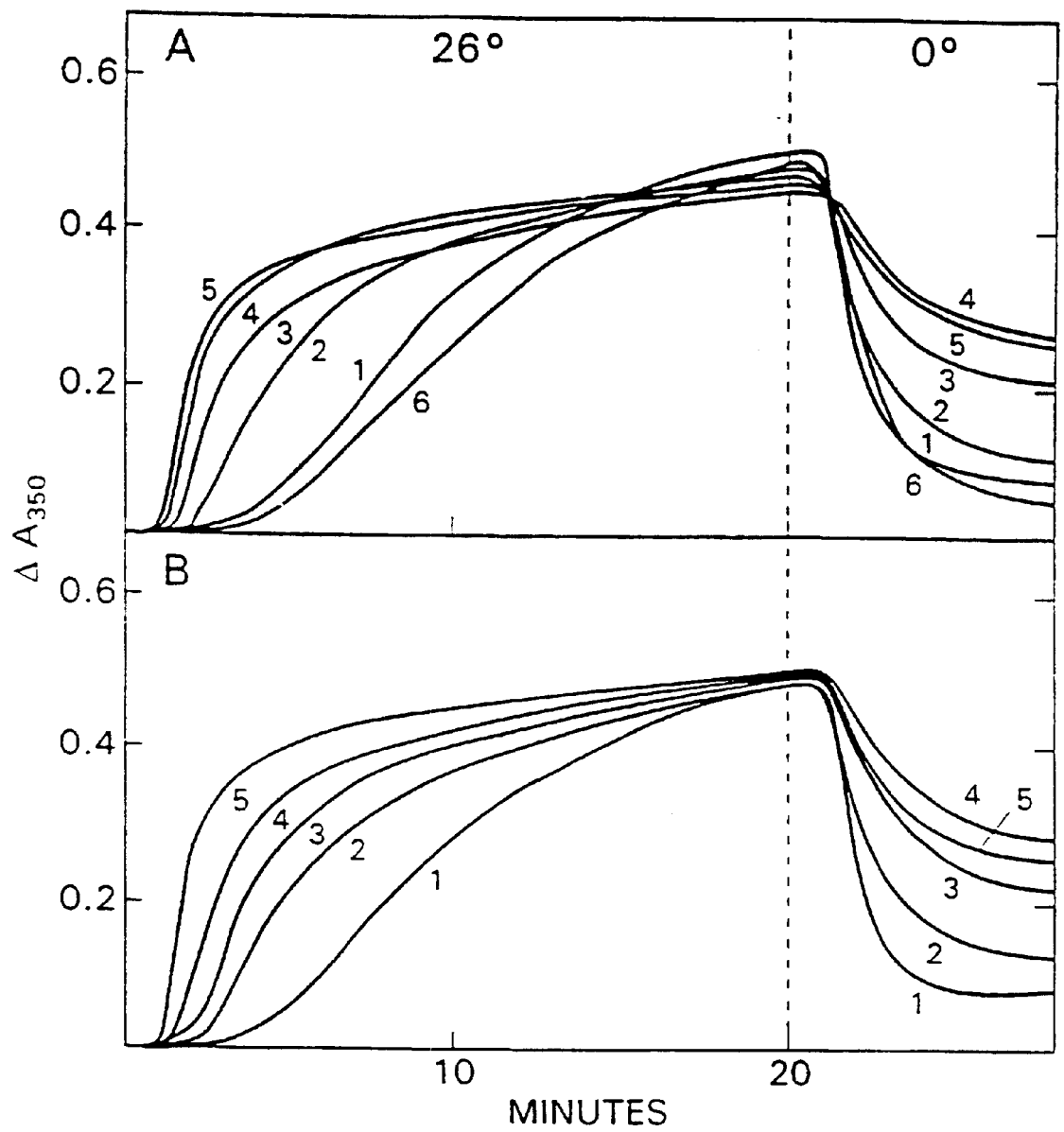
FIG. 4 is a series of turbidimetric curves showing enhancement of glutamate-induced tubulin assembly (A: compounds 13 and 14; B: compound 18) in the absence of MAPs.

As shown in FIG. 4, in experiments with 0.75 mg/ml MAPs and 1.0 mg/ml tubulin, compounds 13 and 18 enhanced tubulin assembly at 25° C., although their activities appeared to be quantitatively lower than had been the case in the glutamate reaction condition. A progressive increase in activity with up to 40 μM agent was seen with both compounds (data presented in full only for compound 13), and at all concentrations compound 18 was less stimulatory than 13 (FIG. 4 presents data with compound 18 only at 10 μM). In addition, FIG. 4 demonstrates the effect of 10 μM paclitaxel on the assembly reaction. With a temperature jump directly from 0 to 25° C., the assembly reaction with paclitaxel was much more extensive than that with compound 13. In part this could be attributed to assembly stimulated by paclitaxel that occurred prior to temperature equilibration, and this could be clearly demonstrated by adding a 10° C. step to the reaction sequence, as was done in the experiment presented in FIG. 4.

It was possible that compounds 13 and 18 were not actually acting like paclitaxel in enhancing microtubule assembly and in stabilizing the microtubules formed in the course of the turbidity studies shown in FIG. 4, but that these agents were causing formation of polymers of aberrant morphology and temperature stability different from microtubules, such as occurs with vinca alkaloids. Polymer morphology was examined by electron microscopy. With compound 13 abundant microtubules were formed that were indistinguishable from those formed in the absence of drug. Even more important, when the reaction mixtures were returned to 0° C. for 15 min, no microtubules were visualized on grids prepared from the reaction mixture without drug. In the presence of 40 μM 13 (FIG. 5) or 10 μM paclitaxel abundant cold stable microtubules were observed.

When either MAPs or GTP was omitted from the reaction mixture, with 10 μM tubulin no reaction occurred with either no drug or 40 μM compound 13. In contrast, with 10 μM paclitaxel a reaction was observed in both cases.

Quantitation of the Effects of Paclitaxel and Compound 13 on Tubulin Polymerization.

FIG. 4: Each reaction mixture contained 0.8 M glutamate (pH 6.6), 0.4 mM GTP, 12 μM (1.2 mg/ml) tubulin, 4% (v/v) dimethyl sulfoxide, and compound 13 or 18 as indicated. Baselines were established at 0°, and at time zero the temperature controller was set at 26°. At the time indicated by the dashed line, the temperature controller was set at 0°. A. Curve 1, no drug; curve 2, 2 μM compound 13; curve 3, 5 μM 7; curve 4, 10 μM 7; curve 5, 40 μM 7; curve 6, 40 μM 14. B. Curve 1, no drug; curve 2, 2 μM compound 18; curve 3, 5 μM 18; curve 4, 10 μM 18; curve 5, 40 μM 18.

Figure 5:
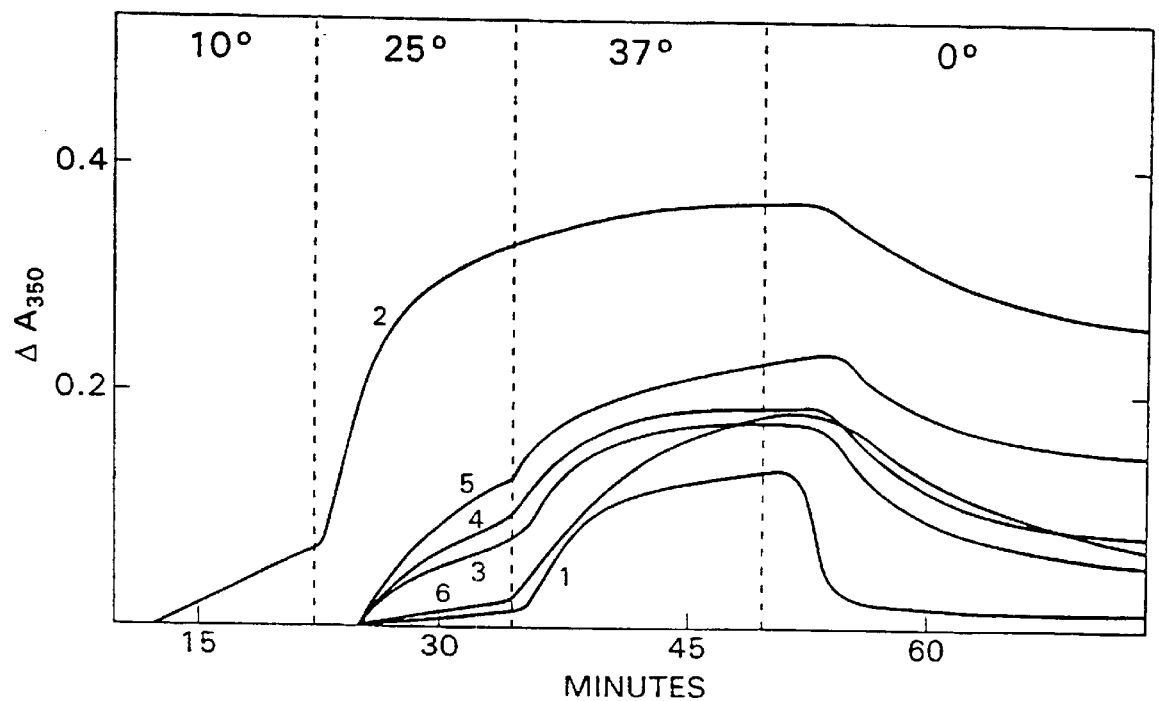
FIG. 5 is a series of turbidimetric curves showing enhancement of MAP-induced tubulin assembly by paclitaxel (curve 2), compound 13 (curves 3–5), and compound 18 (curve 6), in the presence of MAPs.

FIG. 5: Each reaction mixture contained 0.1 M Mes (pH 6.9 with NaOH in 0.5 M stock solution), 0.1 mM GTP, 10 μM (1.0 mg/ml) tubulin, 0.75 mg/ml heat-treated MAPs, 4% dimethyl sulfoxide, and drug as indicated. Baselines were established at 0°, with drug added last, and the cuvette contents were observed for 10 min. There was no change in turbidity in any reaction mixture. At this point the temperature controller was set at 10°, and subsequent temperature changes, as indicated, were made at the times indicated by the vertical dashed lines. Curve 1, no drug; curve 2, 10 μM paclitaxel; curve 3, 10 μM compound 13; curve 4, 20 μM 7; curve 5, 40 μM 7; curve 6, 10 μM compound 18.

It is clear from FIG. 5 that the activities of 13 and 18 are significantly less than that of paclitaxel. It would be desirable to quantitate this difference, however 13 only minimally inhibits the binding of [$^3$H]paclitaxel to tubulin polymer, and 13 was inactive in room temperature glutamate-dependent assay systems where no polymerization reaction occurs in the absence of drug.

Figure 6:
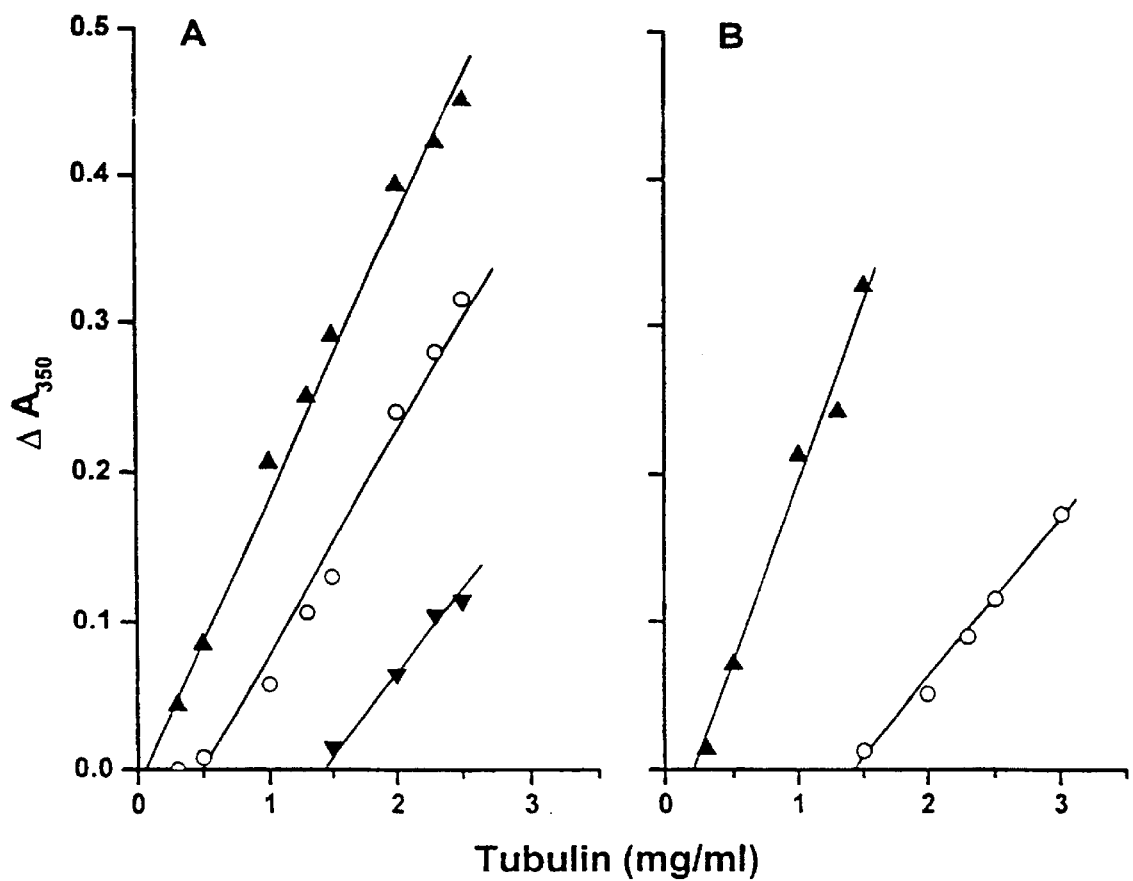
FIG. 6 presents critical concentrations, obtained at 30° C., of tubulin with paclitaxel and compound 13. A: MAPs -and GTP-dependent assembly without drug and in the presence of 10 μM paclitaxel or 10 μM 13. B: GTP-dependent, MAP-independent assembly with 10 μM paclitaxel or 10 μM 13.

With 10 μM 13 and 40 μM tubulin, assembly of microtubules was observed without MAPs but not without GTP. Measurement of the critical concentration with and without MAPs with paclitaxel, and again with 13, was therefore carried out to provide some idea of the comparative activity of these agents. The data are presented in FIG. 6, which yield critical concentrations, obtained at 30° C., of 1.4, 0.06, and 0.50 mg/ml for MAP-and GTP-dependent assembly without drug and in the presence of 10 μM paclitaxel or 10 μM 13, respectively, and 0.20 and 1.4 mg/ml for GTP-dependent, MAP-independent assembly with 10 μM paclitaxel or 10 μM 13. No reaction occurred without drug at tubulin concentrations up to 4 mg/ml. (A constant weight ratio of MAPs to tubulin of 1:3 was used, because the suboptimal concentration of MAPs caused greater differences in the critical concentrations obtained.) Reaction mixtures (0.25 ml) contained 0.1 M Mes (pH 6.9), 100 μM GTP, 4% dimethyl sulfoxide, the indicated tubulin concentration (with heat-treated MAPs in 1:3 weight ratio to the tubulin, panel A only), and either 10 μM paclitaxel (▲), 10 μM compound 13 (○), or no drug (▼). Cuvette contents were equilibrated at 0°, drugs were added, temperature was jumped to 30° (about one min), and the turbidity changes after a 20 min incubation measured.

At first glance, the data suggest that the affinity of paclitaxel for tubulin polymers is 7–8-fold greater than that of compound 13, but this method may significantly underestimate the difference between the two compounds. Previous observations with paclitaxel analogs indicate that differences between compounds are magnified in restrictive reaction conditions and minimized in favorable reaction conditions. For example, it has been found that sarcodictyin A is significantly less potent than paclitaxel in its interactions with tubulin under restrictive reaction conditions, and it only weakly inhibits the binding of paclitaxel to tubulin polymer (Hamel et al., Biochemistry 38:5490–5498 (1999)). However, under favorable reaction conditions (room temperature) the quantitative difference between paclitaxel and sarcodictyin A was only 2.5-fold. Compound 13 was inactive in this room temperature assay. The critical concentration with 10 μM sarcodictyin A under the reaction conditions shown in FIG. 6B is 1.0 mg/ml in the GTP-only system. Relative order of compound activity thus persists, with sarcodictyin A being about 5-fold less active than paclitaxel and 40% more active than 13.

Cytotoxicity Against Tumor cells in Vitro.

The compounds of the invention were tested for inhibition of cell growth in the established tumor cell screen of the National Cancer Institute Developmental Therapeutics Program. See Boyd et al., *Drug Dev. Res.*, 34:91–109 (1995). Results are presented in Table 1 as the "MGM" values (mean graph midpoint, in µM, for all cell lines tested).

TABLE 1

| Compound No. | Cytotoxicity (MGM µM) | Tubulin polymerization inhibition (IC$_{50}$ µM) |
|---|---|---|
| 9 | n.t. | >40 |
| 10 | n.t. | >40 |
| 11 | n.t. | 1.3 |
| 12 | n.t. | >40 |
| 13 | n.t. | * |
| 14 | n.t. | >40 |
| 18 | n.t. | * |
| 19 | n.t. | >40 |
| 27 | 0.567 | >40 |
| 28 | n.t. | n.t |
| 29 | 16.2 | 4 |
| 30 | 49.0 | >40 |
| 31 | 38.0 | >40 |
| 32 | 35.5 | 25 |
| 33 | 50.1 | >40 | n.t.: not tested
*: Accelerates tubulin polymerization

While the examples presented above describe a number of embodiments of this invention, it is apparent to those skilled in the relevant arts that the compounds, compositions, and methods of this invention can be altered to provide alternative embodiments, and equivalent compositions and methods, which nonetheless remain within the scope of this invention. Therefore, it will be appreciated that the present invention is not limited in scope by the specific embodiments described above, which are intended only as illustrations of individual aspects of the invention. In particular, modifications which are obvious to those of ordinary skill in the art are intended to be within the spirit and scope of the following claims.

We claim:

1. A compound of formula

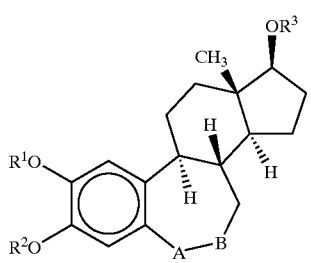

wherein:
A is selected from the group consisting of CH$_2$, NR$^4$, C=O, C=NOH, CHNHCR$^5$ and CHOH;
B is selected from the group consisting of CH$_2$ and C=O;
R$^1$ is selected from the group consisting of H, methyl, ethyl, n-propyl, i-propyl, cyclopropyl, cyclopropylmethyl, 1-propenyl, allyl, and vinyl;
R$^2$ and R$^4$ are selected from the group consisting of H, methyl, ethyl, n-propyl, i-propyl, acetyl, propionyl, butyryl, cyclopropanecarbonyl, and isobutyryl;
R$^3$ is selected from the group consisting of H, acetyl, propionyl, butyryl, cyclopropanecarbonyl, and isobutyryl;
and R5 is selected from the group consisting of H, methyl, ethyl, n-propyl, i-propyl, acetyl, propionyl, butyryl, cyclopropanecarbonyl, and isobutyryl.

2. The compound of claim 1 wherein R$^1$ is selected from the group consisting of H, methyl, and ethyl.

3. The compound of claim 2 wherein R$^2$ is selected from the group consisting of H, acetyl, propionyl, butyryl, and isobutyryl.

4. The compound of claim 1 wherein R$^1$ is ethyl and R$^2$ is H or acetyl.

5. The compound of claim 1 wherein R$^3$ is acetyl or propionyl.

6. The compound of claim 2 wherein R$^3$ is acetyl or propionyl.

7. The compound of claim 3 wherein R$^3$ is acetyl or propionyl.

8. The compound of claim 4 wherein R$^3$ is acetyl or propionyl.

9. The compound of any one of claims 5–8 wherein R3 is acetyl.

10. The compound of any one of claims 1–8 wherein A is CH$_2$.

11. The compound of any one of claims 1–8 wherein A is C=O.

12. The compound of any one of claims 1–8 wherein A is NR$^4$.

13. The compound of claim 12 wherein B is C=O.

14. The compound of claim 12 wherein R$^4$ is selected from the group consisting of H, acetyl, and propionyl.

15. The compound of claim 14 wherein B is C=O.

16. The compound of any one of claims 1–8 wherein A is CHNHR$^4$.

17. The compound of claim 16 wherein R$^4$ is selected from the group consisting of H, acetyl, and propionyl.

18. The compound of claim 9 wherein A is CH$_2$.

19. The compound of claim 9 wherein A is C=O.

20. A method for treating a disease characterized by undesirable mitosis and/or undesirable angiogenesis, said method comprising administering to a mammal having said disease an effective amount of a compound of the formula below:

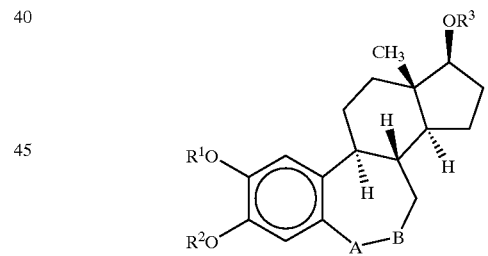

wherein:
A is selected from the group consisting of CH$_2$, NR$^4$, C=O, C=NOH, CHNHCR$^5$ and CHOH;
B is selected from the group consisting of CH$_2$ and C=O;
R$^1$ is selected from the group consisting of H, methyl, ethyl, n-propyl, i-propyl, cyclopropyl, cyclopropylmethyl, 1-propenyl, allyl, and vinyl;
R$^2$ and R$^4$ are selected from the group consisting of H, methyl, ethyl, n-propyl, i-propyl, acetyl, propionyl, butyryl, cyclopropanecarbonyl, and isobutyryl;
R$^3$ is selected from the group consisting of H, acetyl, propionyl, butyryl, cyclopropanecarbonyl, and isobutyryl;
and R5 is selected from the group consisting of H, methyl, ethyl, n-propyl, i-propyl, acetyl, propionyl, butyryl, cyclopropanecarbonyl, and isobutyryl.

21. The method of claim 20 wherein $R^1$ is selected from the group consisting of H, methyl, and ethyl.

22. The method of claim 21 wherein $R^2$ is selected from the group consisting of H, acetyl, propionyl, butyryl, and isobutyryl.

23. The method of claim 20 wherein $R^1$ is ethyl and $R^2$ is H or acetyl.

24. The method of claim 20 wherein $R^3$ is acetyl or propionyl.

25. The method of claim 21 wherein $R^3$ is acetyl or propionyl.

26. The method of claim 22 wherein $R^3$ is acetyl or propionyl.

27. The method of claim 23 wherein $R^3$ is acetyl or propionyl.

28. The method of any one of claims 24–27 wherein R3 is acetyl.

29. The method of any one of claims 20–27 wherein A is $CH_2$.

30. The method of any one of claims 20–27 wherein A is C=O.

31. The method of any one of claims 20–27 wherein A is $NR^4$.

32. The method of claim 21 wherein B is C=O.

33. The method of claim 21 wherein $R^4$ is selected from the group consisting of H, acetyl, and propionyl.

34. The method of claim 23 wherein B is C=O.

35. The method of any one of claims 20–27 wherein A is $CHNHR^4$.

36. The method of claim 25 wherein $R^4$ is selected from the group consisting of H, acetyl, and propionyl.

37. The method of claim 28 wherein A is $CH_2$.

38. The method of claim 28 wherein A is C=O.

39. The method of any one of claims 20–27 wherein the disease is cancer.

\* \* \* \* \*

UNITED STATES PATENT AND TRADEMARK OFFICE
CERTIFICATE OF CORRECTION

PATENT NO. : 6,696,436 B1  
DATED : February 24, 2004  
INVENTOR(S) : Hamel, Ernest et al.

It is certified that error appears in the above-identified patent and that said Letters Patent is hereby corrected as shown below:

Column 1,
Line 8, please add the following statement:
-- STATEMENT REGARDING FEDERALLY SPONSORED RESEARCH AND DEVELOPMENT
   This invention was made in part with Government support under Grant Number CM067260 awarded by the National Institutes of Health. The Government may have certain rights in this invention. --

Signed and Sealed this

Second Day of August, 2005

JON W. DUDAS
*Director of the United States Patent and Trademark Office*